United States Patent
Gramnaes (10) Patent No.: US 9,717,606 B2
(45) Date of Patent: Aug. 1, 2017

(54) COMBINED ACTIVE AND PASSIVE LEG PROSTHESIS SYSTEM AND A METHOD FOR PERFORMING A MOVEMENT WITH SUCH A SYSTEM

(71) Applicant: Össur hf, Reykjavik (IS)

(72) Inventor: Lisa Gramnaes, Göteborg (SE)

(73) Assignee: Össur hf, Reykjavik (IS)

( * ) Notice: Subject to any disclaimer, the term of this patent is extended or adjusted under 35 U.S.C. 154(b) by 0 days.

(21) Appl. No.: 14/743,021

(22) Filed: Jun. 18, 2015

(65) Prior Publication Data

US 2015/0320573 A1    Nov. 12, 2015

Related U.S. Application Data

(63) Continuation of application No. 13/846,695, filed on Mar. 18, 2013, now Pat. No. 9,066,819, which is a (Continued)

(30) Foreign Application Priority Data

Apr. 19, 2005 (SE) ...................................... 0500882

(51) Int. Cl.
*A61F 2/64* (2006.01)
*A61F 2/48* (2006.01)
(Continued)

(52) U.S. Cl.
CPC .................. *A61F 2/68* (2013.01); *A61F 2/64* (2013.01); *A61F 2/6607* (2013.01); *A61F 2/70* (2013.01);
(Continued)

(58) Field of Classification Search
CPC ............................................... A61F 2002/745
See application file for complete search history.

(56) References Cited

U.S. PATENT DOCUMENTS 2,568,051 A    9/1951 Catranis
2,619,652 A    12/1952 Vesper
(Continued)

FOREIGN PATENT DOCUMENTS

CH    543 277    12/1973
CN    2043873    9/1989
(Continued)

OTHER PUBLICATIONS

Abbas et al., "Neural Network Control of Functional Neuromuscular Stimulation Systems: Computer Stimulation Studies," IEEE Transactions on Biomedical Engineering, vol. 42, No. 11, Nov. 1995, pp. 1117-1127.
(Continued)

*Primary Examiner* — Jacqueline Woznicki
(74) *Attorney, Agent, or Firm* — Knobbe, Martens, Olson & Bear, LLP (57) ABSTRACT

A lower limb prosthesis system and a method of controlling the prosthesis system to replace a missing lower extremity of an individual and perform a gait cycle are disclosed. The prosthesis system has a controller, one or more sensors, a prosthetic foot, and a movable ankle joint member coupled to the prosthetic foot. The movable ankle joint member comprises a hydraulic damping system that provides the ankle joint member damping resistance. The controller varies the damping resistance by providing volumetric flow control to the hydraulic damping system based on sensor data. In one embodiment, the hydraulic damping system comprises a hydraulic piston cylinder assembly, hydraulic fluid, and a valve to regulate the fluid. In one embodiment, the controller alters the damping resistance by modulating the valve to vary the hydraulic fluid flow within the hydraulic piston cylinder assembly of the movable ankle joint member based on sensor data.

8 Claims, 8 Drawing Sheets

Related U.S. Application Data continuation of application No. 11/887,374, filed as application No. PCT/SE2006/000445 on Apr. 18, 2006, now Pat. No. 8,814,949.

(51) Int. Cl.

| | | |
|---|---|---|
| *A61F 2/72* | (2006.01) | |
| *A61F 2/68* | (2006.01) | |
| *A61F 2/70* | (2006.01) | |
| *A61F 2/66* | (2006.01) | |
| *A61F 2/50* | (2006.01) | |
| *A61F 2/60* | (2006.01) | |
| *A61F 2/74* | (2006.01) | |
| *A61F 2/76* | (2006.01) | |

(52) U.S. Cl.
CPC . *A61F 2/66* (2013.01); *A61F 2/72* (2013.01); *A61F 2002/5038* (2013.01); *A61F 2002/607* (2013.01); *A61F 2002/6614* (2013.01); *A61F 2002/6818* (2013.01); *A61F 2002/704* (2013.01); *A61F 2002/705* (2013.01); *A61F 2002/741* (2013.01); *A61F 2002/745* (2013.01); *A61F 2002/748* (2013.01); *A61F 2002/763* (2013.01); *A61F 2002/764* (2013.01); *A61F 2002/7625* (2013.01); *A61F 2002/7655* (2013.01)

(56) References Cited

U.S. PATENT DOCUMENTS

| | | |
|---|---|---|
| 2,859,451 A | 11/1958 | Mauch |
| 3,316,558 A | 5/1967 | Mortensen |
| 3,417,409 A | 12/1968 | Prahl |
| 3,501,776 A | 3/1970 | Beeker et al. |
| 3,659,294 A | 5/1972 | Glabiszewski |
| 3,701,368 A | 10/1972 | Stern |
| 3,791,375 A | 2/1974 | Pfeifer |
| 3,820,168 A | 6/1974 | Horvath |
| 3,866,246 A | 2/1975 | Seamone et al. |
| 3,871,032 A | 3/1975 | Karas |
| 3,995,324 A | 12/1976 | Burch |
| 4,005,496 A | 2/1977 | Wilkes |
| 4,023,215 A | 5/1977 | Moore |
| 4,030,141 A | 6/1977 | Graupe |
| 4,064,569 A | 12/1977 | Campbell |
| 4,065,815 A | 1/1978 | Sen-Jung |
| 4,100,918 A | 7/1978 | Glancy |
| 4,179,759 A | 12/1979 | Smith |
| 4,209,860 A | 7/1980 | Graupe |
| 4,212,087 A | 7/1980 | Mortensen |
| 4,310,932 A | 1/1982 | Nader et al. |
| 4,314,379 A | 2/1982 | Tanie et al. |
| 4,354,676 A | 10/1982 | Ariel |
| 4,363,498 A | 12/1982 | Biermann et al. |
| 4,370,977 A | 2/1983 | Mauldin et al. |
| 4,386,891 A | 6/1983 | Riefel et al. |
| 4,387,472 A | 6/1983 | Wilson |
| 4,433,679 A | 2/1984 | Mauldin et al. |
| 4,458,367 A | 7/1984 | May |
| 4,518,307 A | 5/1985 | Bloch |
| 4,521,924 A | 6/1985 | Jacobsen et al. |
| 4,556,956 A | 12/1985 | Dickenson et al. |
| 4,558,704 A | 12/1985 | Petrofsky |
| 4,569,352 A | 2/1986 | Petrofsky et al. |
| 4,578,083 A | 3/1986 | Williams |
| 4,600,357 A | 7/1986 | Coules |
| 4,602,619 A | 7/1986 | Wolf et al. |
| 4,617,920 A | 10/1986 | Carsalade |
| 4,649,934 A | 3/1987 | Fraser et al. |
| 4,657,000 A | 4/1987 | Hepburn |
| 4,657,470 A | 4/1987 | Clarke et al. |
| 4,685,926 A | 8/1987 | Haupt |
| 4,685,927 A | 8/1987 | Haupt |
| 4,711,242 A | 12/1987 | Petrofsky |
| 4,711,450 A | 12/1987 | McArthur |
| 4,726,404 A | 2/1988 | Haber et al. |
| 4,730,625 A | 3/1988 | Fraser et al. |
| 4,760,850 A | 8/1988 | Phillips et al. |
| 4,770,662 A | 9/1988 | Giampapa |
| 4,776,326 A | 10/1988 | Roung et al. |
| 4,776,852 A | 10/1988 | Rubic |
| 4,790,522 A | 12/1988 | Drutchas |
| 4,795,474 A | 1/1989 | Horvath |
| 4,805,455 A | 2/1989 | DelGiorno et al. |
| 4,808,187 A | 2/1989 | Patterson et al. |
| 4,814,661 A | 3/1989 | Ratzlaff et al. |
| 4,838,251 A | 6/1989 | Chignon et al. |
| 4,843,921 A | 7/1989 | Kremer |
| 4,854,428 A | 8/1989 | Horvath |
| 4,865,024 A | 9/1989 | Hensley et al. |
| 4,872,803 A | 10/1989 | Asakawa |
| 4,876,944 A | 10/1989 | Wilson et al. |
| 4,878,913 A | 11/1989 | Aebischer et al. |
| 4,892,554 A | 1/1990 | Robinson |
| 4,893,648 A | 1/1990 | Horvath |
| 4,919,418 A | 4/1990 | Miller |
| 4,928,676 A | 5/1990 | Pansiera |
| 4,944,755 A | 7/1990 | Hennequin et al. |
| 4,958,705 A | 9/1990 | Horvath |
| 4,994,086 A | 2/1991 | Edwards |
| 5,020,790 A | 6/1991 | Beard et al. |
| 5,033,291 A | 7/1991 | Podoloff et al. |
| 5,044,360 A | 9/1991 | Janke |
| 5,062,856 A | 11/1991 | Sawamura et al. |
| 5,062,857 A | 11/1991 | Berringer |
| 5,086,785 A | 2/1992 | Gentile et al. |
| 5,092,902 A | 3/1992 | Adams et al. |
| 5,112,296 A | 5/1992 | Beard et al. |
| 5,112,356 A | 5/1992 | Harris et al. |
| 5,139,525 A | 8/1992 | Kristinsson |
| 5,153,496 A | 10/1992 | LaForge |
| 5,174,168 A | 12/1992 | Takagi et al. |
| 5,181,931 A | 1/1993 | Van de Veen |
| 5,197,488 A | 3/1993 | Kovacevic |
| 5,201,772 A | 4/1993 | Maxwell |
| 5,217,500 A | 6/1993 | Phillips |
| 5,219,365 A | 6/1993 | Sabolich |
| 5,230,672 A | 7/1993 | Brown et al. |
| 5,246,465 A | 9/1993 | Rincoe et al. |
| 5,252,102 A | 10/1993 | Singer et al. |
| 5,252,901 A | 10/1993 | Ozawa et al. |
| 5,253,656 A | 10/1993 | Rincoe et al. |
| 5,265,890 A | 11/1993 | Balsells |
| 5,277,281 A | 1/1994 | Carlson et al. |
| 5,282,460 A | 2/1994 | Boldt |
| 5,284,330 A | 2/1994 | Carlson et al. |
| 5,314,498 A | 5/1994 | Gramnaes |
| 5,323,650 A | 6/1994 | Fullen et al. |
| 5,327,790 A | 7/1994 | Levin et al. |
| 5,336,269 A | 8/1994 | Smits |
| 5,357,696 A | 10/1994 | Gray et al. |
| 5,376,128 A | 12/1994 | Bozeman, Jr. |
| 5,376,133 A | 12/1994 | Gramnaes |
| 5,376,137 A | 12/1994 | Shorter et al. |
| 5,382,373 A | 1/1995 | Carlson et al. |
| 5,383,939 A * | 1/1995 | James .............. A61F 2/64 188/317 |
| 5,394,132 A | 2/1995 | Poil |
| 5,397,287 A | 3/1995 | Lindfors |
| 5,398,917 A | 3/1995 | Carlson et al. |
| 5,405,407 A | 4/1995 | Kodama et al. |
| 5,405,409 A | 4/1995 | Knoth |
| 5,405,410 A | 4/1995 | Arbogast et al. |
| 5,405,510 A | 4/1995 | Betts |
| 5,408,873 A | 4/1995 | Schmidt et al. |
| 5,413,611 A | 5/1995 | Haslam, II et al. |
| 5,422,558 A | 6/1995 | Stewart |
| 5,437,611 A | 8/1995 | Stern |
| 5,443,521 A | 8/1995 | Knoth et al. |
| 5,443,524 A | 8/1995 | Sawamura et al. |
| 5,443,528 A | 8/1995 | Allen |
| 5,458,655 A | 10/1995 | Bozeman, Jr. |

(56) References Cited

U.S. PATENT DOCUMENTS

| | | |
|---|---|---|
| 5,472,412 A | 12/1995 | Knoth |
| 5,476,441 A | 12/1995 | Durfee et al. |
| 5,480,454 A | 1/1996 | Bozeman, Jr. |
| 5,504,415 A | 4/1996 | Podrazhansky et al. |
| D372,536 S | 8/1996 | Grifka |
| 5,545,232 A | 8/1996 | Van de Veen |
| 5,545,233 A | 8/1996 | Fitzlaff |
| 5,551,525 A | 9/1996 | Pack et al. |
| 5,563,458 A | 10/1996 | Ericson |
| 5,566,479 A | 10/1996 | Gray et al. |
| 5,571,205 A | 11/1996 | James |
| 5,571,210 A | 11/1996 | Lindh |
| 5,571,212 A | 11/1996 | Cornelius |
| 5,571,213 A | 11/1996 | Allen |
| 5,583,476 A | 12/1996 | Langford et al. |
| 5,586,557 A | 12/1996 | Nelson et al. |
| 5,624,389 A | 4/1997 | Zepf |
| 5,642,096 A | 6/1997 | Leyerer et al. |
| 5,645,590 A | 7/1997 | Van de Veen |
| 5,645,752 A | 7/1997 | Weiss et al. |
| 5,650,704 A | 7/1997 | Pratt et al. |
| 5,656,915 A | 8/1997 | Eaves |
| D383,542 S | 9/1997 | Wellershaus et al. |
| 5,662,693 A | 9/1997 | Johnson et al. |
| 5,670,077 A | 9/1997 | Carlson et al. |
| 5,678,448 A | 10/1997 | Fullen et al. |
| 5,683,615 A | 11/1997 | Munoz |
| 5,695,527 A | 12/1997 | Allen |
| 5,704,945 A | 1/1998 | Wagner et al. |
| 5,704,946 A | 1/1998 | Greene |
| 5,711,746 A | 1/1998 | Carlson |
| 5,728,170 A | 3/1998 | Becker et al. |
| 5,728,174 A | 3/1998 | Fitzlaff |
| 5,746,774 A | 5/1998 | Kramer |
| 5,749,533 A | 5/1998 | Daniels |
| 5,755,812 A | 5/1998 | Becker et al. |
| 5,755,813 A | 5/1998 | Krukenberg |
| 5,779,735 A | 7/1998 | Molino |
| 5,800,561 A | 9/1998 | Rodriguez |
| 5,800,568 A | 9/1998 | Atkinson et al. |
| 5,810,752 A | 9/1998 | Grifka |
| 5,823,309 A | 10/1998 | Gopalswamy et al. |
| D402,368 S | 12/1998 | Holzapfel |
| 5,842,547 A | 12/1998 | Carlson et al. |
| D407,490 S | 3/1999 | Zepf et al. |
| 5,878,851 A | 3/1999 | Carlson et al. |
| 5,888,212 A | 3/1999 | Petrofsky et al. |
| 5,888,213 A | 3/1999 | Sears et al. |
| 5,888,236 A | 3/1999 | Van de Veen |
| 5,888,239 A | 3/1999 | Wellershaus et al. |
| 5,888,246 A | 3/1999 | Gow |
| 5,893,891 A | 4/1999 | Zahedi |
| 5,895,430 A | 4/1999 | O'Connor |
| 5,899,869 A | 5/1999 | Barrack, Jr. et al. |
| 5,900,184 A | 5/1999 | Weiss et al. |
| 5,906,767 A | 5/1999 | Karol et al. |
| 5,919,149 A | 7/1999 | Allum |
| 5,929,332 A | 7/1999 | Brown |
| 5,941,913 A | 8/1999 | Woolnough et al. |
| 5,947,238 A | 9/1999 | Jolly et al. |
| 5,948,021 A | 9/1999 | Radcliffe |
| 5,955,667 A | 9/1999 | Fyfe |
| 5,957,981 A | 9/1999 | Gramnaes |
| 5,960,918 A | 10/1999 | Moser et al. |
| 5,967,273 A | 10/1999 | Hampton |
| 5,972,035 A | 10/1999 | Blatchford |
| 5,982,156 A | 11/1999 | Weimer et al. |
| 5,998,930 A | 12/1999 | Upadhyay et al. |
| 6,006,412 A | 12/1999 | Bergmann et al. |
| 6,007,582 A | 12/1999 | May |
| RE36,521 E | 1/2000 | Hiemisch |
| 6,027,664 A | 2/2000 | Weiss et al. |
| 6,039,091 A | 3/2000 | Rodgers et al. |
| 6,061,577 A | 5/2000 | Andrieu et al. |
| 6,080,123 A | 6/2000 | Pansiera |
| 6,086,616 A | 7/2000 | Okuda et al. |
| 6,091,977 A | 7/2000 | Tarjan et al. |
| 6,093,162 A | 7/2000 | Fairleigh et al. |
| 6,095,486 A | 8/2000 | Ivers et al. |
| 6,113,642 A | 9/2000 | Petrofsky et al. |
| 6,117,177 A | 9/2000 | Chen et al. |
| 6,129,690 A | 10/2000 | Hamlin et al. |
| 6,129,766 A | 10/2000 | Johnson et al. |
| 6,139,586 A | 10/2000 | Wagner et al. |
| 6,151,624 A | 11/2000 | Teare et al. |
| 6,164,967 A | 12/2000 | Sale |
| 6,165,226 A | 12/2000 | Wagner |
| 6,168,634 B1 | 1/2001 | Schmitz |
| 6,183,425 B1 | 2/2001 | Whalen et al. |
| 6,185,614 B1 | 2/2001 | Cuomo et al. |
| 6,187,051 B1 | 2/2001 | Gerad van de Veen |
| D439,339 S | 3/2001 | Sawatzki |
| 6,195,921 B1 | 3/2001 | Truong |
| 6,206,932 B1 | 3/2001 | Johnson |
| 6,206,933 B1 | 3/2001 | Shorter et al. |
| 6,206,934 B1 | 3/2001 | Phillips |
| 6,241,775 B1 | 6/2001 | Blatchford |
| D446,304 S | 8/2001 | Sawatzki |
| 6,301,964 B1 | 10/2001 | Fyfe et al. |
| 6,342,076 B1 | 1/2002 | Lundborg |
| 6,350,286 B1 | 2/2002 | Atkinson et al. |
| 6,352,144 B1 | 3/2002 | Brooks |
| 6,361,570 B1 | 3/2002 | Gow |
| 6,373,152 B1 | 4/2002 | Wang et al. |
| 6,395,193 B1 | 5/2002 | Kintz et al. |
| 6,409,695 B1 | 6/2002 | Connelly |
| 6,423,098 B1 | 7/2002 | Biedermann |
| 6,425,925 B1 | 7/2002 | Grundei |
| 6,430,843 B1 | 8/2002 | Potter et al. |
| 6,436,149 B1 | 8/2002 | Rincoe |
| 6,443,993 B1 | 9/2002 | Koniuk |
| 6,443,995 B1 | 9/2002 | Townsend et al. |
| 6,451,481 B1 | 9/2002 | Lee et al. |
| 6,485,519 B2 | 11/2002 | Meyers et al. |
| 6,494,039 B2 | 12/2002 | Pratt et al. |
| 6,500,210 B1 | 12/2002 | Sabolich et al. |
| 6,513,381 B2 | 2/2003 | Fyfe et al. |
| 6,517,585 B1 | 2/2003 | Zahedi et al. |
| 6,517,828 B1 | 2/2003 | Fyfe et al. |
| 6,522,266 B1 | 2/2003 | Soehren et al. |
| 6,537,322 B1 | 3/2003 | Johnson et al. |
| 6,574,655 B1 | 6/2003 | Libert et al. |
| 6,587,728 B2 | 7/2003 | Fang et al. |
| 6,589,287 B2 | 7/2003 | Lundborg |
| 6,599,439 B2 | 7/2003 | Iregar et al. |
| 6,602,295 B1 | 8/2003 | Doddroe et al. |
| 6,610,101 B2 | 8/2003 | Herr et al. |
| 6,613,097 B1 | 9/2003 | Cooper |
| 6,645,252 B2 | 11/2003 | Asai et al. |
| 6,663,673 B2 | 12/2003 | Christensen |
| 6,671,531 B2 | 12/2003 | Al-Ali et al. |
| 6,679,920 B2 | 1/2004 | Biedermann et al. |
| 6,695,885 B2 | 2/2004 | Schulman et al. |
| 6,719,806 B1 | 4/2004 | Zahedi et al. |
| 6,733,180 B2 | 5/2004 | Nakamura |
| 6,740,123 B2 | 5/2004 | Davalli et al. |
| 6,740,125 B2 | 5/2004 | Mosler |
| 6,743,260 B2 | 6/2004 | Townsend et al. |
| 6,755,870 B1 | 6/2004 | Biedermann et al. |
| 6,761,743 B1 | 7/2004 | Johnson |
| 6,764,520 B2 | 7/2004 | Deffenbaugh et al. |
| 6,770,045 B2 | 8/2004 | Naft et al. |
| 6,780,343 B2 | 8/2004 | Hata et al. |
| 6,805,677 B2 | 10/2004 | Simmons |
| 6,811,571 B1 | 11/2004 | Phillips |
| 6,813,582 B2 | 11/2004 | Levi et al. |
| D499,487 S | 12/2004 | Bédard et al. |
| D501,925 S | 2/2005 | Bédard et al. |
| 6,855,170 B2 | 2/2005 | Gramnäs |
| 6,875,241 B2 | 4/2005 | Christensen |
| 6,876,135 B2 | 4/2005 | Pelrine et al. |
| 6,918,308 B2 | 7/2005 | Biedermann |
| 6,955,692 B2 | 10/2005 | Grundei |
| 6,966,882 B2 | 11/2005 | Horst |

(56) References Cited

U.S. PATENT DOCUMENTS

| | | |
|---|---|---|
| 6,966,933 B2 | 11/2005 | Christensen |
| 7,025,792 B2 | 4/2006 | Collier |
| 7,029,500 B2 | 4/2006 | Martin |
| 7,042,197 B2 | 5/2006 | Turner et al. |
| 7,063,727 B2 | 6/2006 | Phillips et al. |
| 7,066,896 B1 | 6/2006 | Kiselik |
| 7,101,487 B2 | 9/2006 | Hsu et al. |
| 7,118,601 B2 | 10/2006 | Yasui |
| 7,131,998 B2 | 11/2006 | Pasolini |
| 7,137,998 B2 | 11/2006 | Bédard et al. |
| 7,147,667 B2 | 12/2006 | Bédard et al. |
| 7,164,967 B2 | 1/2007 | Etienne-Cummings et al. |
| 7,182,738 B2 | 2/2007 | Bonutti et al. |
| 7,198,071 B2 | 4/2007 | Bisbee, III et al. |
| 7,279,009 B2 | 10/2007 | Herr et al. |
| 7,295,892 B2 | 11/2007 | Herr et al. |
| 7,308,333 B2 | 12/2007 | Kern et al. |
| 7,313,463 B2 | 12/2007 | Herr et al. |
| 7,314,490 B2 | 1/2008 | Bédard et al. |
| 7,396,337 B2 | 7/2008 | McBean et al. |
| 7,410,338 B2 | 8/2008 | Schiele et al. |
| 7,410,471 B1 | 8/2008 | Campbell et al. |
| 7,410,472 B2 | 8/2008 | Yakimovich et al. |
| 7,431,737 B2 | 10/2008 | Ragnarsdottir et al. |
| 7,455,696 B2 | 11/2008 | Bisbee, III et al. |
| 7,462,201 B2 | 12/2008 | Christensen |
| 7,503,900 B2 | 3/2009 | Goswami |
| 7,520,904 B2 | 4/2009 | Christensen |
| 7,531,006 B2 | 5/2009 | Clausen et al. |
| 7,552,664 B2 | 6/2009 | Bulatowicz |
| 7,575,602 B2 | 8/2009 | Amirouche et al. |
| 7,588,604 B2 | 9/2009 | Okuda |
| 7,637,957 B2 | 12/2009 | Ragnarsdottir et al. |
| 7,637,959 B2 | 12/2009 | Clausen et al. |
| 7,641,700 B2 | 1/2010 | Yasui |
| 7,655,050 B2 | 2/2010 | Palmer et al. |
| 7,691,154 B2 | 4/2010 | Asgeirsson et al. |
| 7,736,394 B2 | 6/2010 | Bédard et al. |
| 7,794,505 B2 | 9/2010 | Clausen et al. |
| 7,799,091 B2 | 9/2010 | Herr et al. |
| 7,811,333 B2 | 10/2010 | Jónsson et al. |
| 7,811,334 B2 | 10/2010 | Ragnarsdottir et al. |
| 7,815,689 B2 | 10/2010 | Bédard et al. |
| 7,862,620 B2 | 1/2011 | Clausen et al. |
| 7,867,284 B2 | 1/2011 | Bédard et al. |
| 7,867,285 B2 | 1/2011 | Clausen et al. |
| 7,896,927 B2 | 3/2011 | Clausen et al. |
| 7,918,808 B2 | 4/2011 | Simmons |
| 7,942,935 B2 | 5/2011 | Iversen et al. |
| 7,955,398 B2 | 6/2011 | Bédard et al. |
| 8,007,544 B2 | 8/2011 | Jonsson et al. |
| 8,048,007 B2 | 11/2011 | Roy |
| 8,048,172 B2 | 11/2011 | Jonsson et al. |
| 8,057,550 B2 | 11/2011 | Clausen |
| 8,075,633 B2 | 12/2011 | Herr et al. |
| 8,083,807 B2 | 12/2011 | Auberger et al. |
| 8,087,498 B2 | 1/2012 | Dupuis et al. |
| 8,109,890 B2 | 2/2012 | Kamiar et al. |
| 8,122,772 B2 | 2/2012 | Clausen et al. |
| 8,142,370 B2 | 3/2012 | Weinberg et al. |
| 8,231,687 B2 | 7/2012 | Bédard et al. |
| 8,287,477 B1 | 10/2012 | Herr et al. |
| 8,323,354 B2 | 12/2012 | Bédard et al. |
| 8,628,585 B2 | 1/2014 | Harris et al. |
| 2002/0087216 A1 | 7/2002 | Atkinson et al. |
| 2003/0019700 A1 | 1/2003 | Wittig |
| 2003/0149600 A1 | 8/2003 | Williams |
| 2004/0064195 A1 | 4/2004 | Herr |
| 2004/0083007 A1 | 4/2004 | Molino et al. |
| 2004/0217324 A1 | 11/2004 | Hsu et al. |
| 2005/0070834 A1* | 3/2005 | Herr ............... A61B 5/1038 602/28 |
| 2005/0107889 A1 | 5/2005 | Bédard et al. |
| 2005/0137717 A1 | 6/2005 | Gramnaes |
| 2005/0216097 A1 | 9/2005 | Rifkin |
| 2005/0283257 A1 | 12/2005 | Bisbee et al. |
| 2006/0136072 A1 | 6/2006 | Bisbee et al. |
| 2006/0184280 A1 | 8/2006 | Oddsson et al. |
| 2006/0224247 A1* | 10/2006 | Clausen ............ A61F 2/66 623/24 |
| 2006/0235544 A1* | 10/2006 | Iversen ............ A61F 2/64 623/26 |
| 2006/0249315 A1 | 11/2006 | Herr et al. |
| 2007/0027557 A1 | 2/2007 | Jonsson et al. |
| 2007/0043449 A1 | 2/2007 | Herr et al. |
| 2007/0050044 A1 | 3/2007 | Haynes et al. |
| 2007/0123997 A1 | 5/2007 | Herr et al. |
| 2007/0162152 A1 | 7/2007 | Herr et al. |
| 2008/0046096 A1 | 2/2008 | Bédard et al. |
| 2010/0262260 A1 | 10/2010 | Bédard et al. |
| 2010/0324456 A1 | 12/2010 | Jónsson et al. |
| 2010/0324699 A1 | 12/2010 | Herr et al. |
| 2011/0106274 A1 | 5/2011 | Ragnarsdottir et al. |
| 2011/0130847 A1 | 6/2011 | Bédard et al. |
| 2011/0137429 A1 | 6/2011 | Bédard et al. |
| 2011/0224804 A1 | 9/2011 | Clausen et al. |
| 2012/0016492 A1 | 1/2012 | Clausen |
| 2013/0035769 A1 | 2/2013 | Bédard et al. |

FOREIGN PATENT DOCUMENTS

| | | |
|---|---|---|
| CN | 1215614 | 5/1999 |
| CN | 2400072 Y | 10/2000 |
| DE | 35 43 291 | 6/1987 |
| DE | 39 23 056 | 1/1991 |
| DE | 39 23 057 | 1/1991 |
| DE | 42 29 330 | 3/1994 |
| EP | 0 654 254 | 5/1995 |
| EP | 1 166 726 | 1/2002 |
| EP | 1 169 982 | 1/2002 |
| FR | 2 293 185 | 7/1976 |
| FR | 2 623 086 | 5/1989 |
| FR | 2 816 463 | 5/2002 |
| GB | 2 201 260 | 8/1988 |
| GB | 2 244 006 | 11/1991 |
| GB | 2 260 495 | 4/1993 |
| GB | 2 301 776 | 12/1996 |
| GB | 2 302 949 | 2/1997 |
| GB | 2 338 653 | 12/1999 |
| GB | 2 343 848 | 5/2000 |
| GB | 2 367 753 | 4/2002 |
| JP | 59-032453 | 2/1984 |
| JP | 59-071747 | 4/1984 |
| JP | 60-081530 | 5/1985 |
| JP | 01-244748 | 9/1989 |
| JP | 03-181633 | 8/1991 |
| JP | 04-078337 | 3/1992 |
| JP | 05-161668 | 6/1993 |
| JP | 11-000345 | 1/1999 |
| JP | 11-056885 | 3/1999 |
| JP | 11-215793 | 8/1999 |
| JP | 2001-277175 | 10/2001 |
| JP | 2002-191654 | 7/2002 |
| JP | 2005-500 | 1/2005 |
| KR | 2002-0041137 | 6/2002 |
| SU | 1447366 | 12/1988 |
| WO | WO 94/06374 | 3/1994 |
| WO | WO 94/09727 | 5/1994 |
| WO | WO 95/26171 | 10/1995 |
| WO | WO 96/39110 | 12/1996 |
| WO | WO 96/41599 | 12/1996 |
| WO | WO 97/27822 | 8/1997 |
| WO | WO 98/38951 | 9/1998 |
| WO | WO 99/00075 | 1/1999 |
| WO | WO 99/05991 | 2/1999 |
| WO | WO 99/55261 | 11/1999 |
| WO | WO 00/27318 | 5/2000 |
| WO | WO 01/17466 | 3/2001 |
| WO | WO 02/080825 | 10/2002 |
| WO | WO 03/003953 | 1/2003 |
| WO | WO 03/088373 | 10/2003 |
| WO | WO 2004/092606 | 10/2004 |

(56) References Cited

FOREIGN PATENT DOCUMENTS

| WO | WO 2005/048887 | 6/2005 |
|----|----------------|--------|
| WO | WO 2005/079712 | 9/2005 |

OTHER PUBLICATIONS

Aminian et al., "Estimation of Speed and Incline of Walking Using Neural Network," IEEE Transactions on Instrumentation and Measurement, vol. 44, No. 3, Jun. 1995, pp. 743-746.
Andrews et al., "Hybrid FES Orthosis Incorporating Closed Loop Control and Sensory Feedback," Journal of Biomedical Engineering, vol. 10, Apr. 1988, pp. 189-195.
Bachmann et al., Inertial and Magnetic Tracking of Limb Segment Orientation for Inserting Humans into Synthetic Environments, Naval Postgraduate School: Dissertation, Dec. 2000, pp. 199.
Bar et al., "Adaptive Microcomputer Control of an Artificial Knee in Level Walking," Journal of Biomechanical Engineering, vol. 5, Apr. 1983, pp. 145-150.
Baten et al., "Inertial Sensing in Ambulatory Back Load Estimation," 18th Annual International Conference of the IEEE Engineering in Medicine and Biology Society, Amsterdam, Oct. 31, 1996-Nov. 3, 1996, pp. 497-498.
Blaya, et al., "Adaptive Control of a Variable-Impedance Ankle-Foot Orthosis to Assist Drop-Foot Gait," IEEE Transactions on Neural Systems and Rehabilitation Engineering, vol. 12, No. 1, Mar. 2004, pp. 24-31.
Blaya, "Force-Controllable Ankle Foot Orthosis (AFO) to Assist Drop Foot Gait," Massachusetts Institute of Technology, Thesis, Feb. 2003 (believed to be catalogued on or after Jul. 8, 2003) in 97 pages.
Blumentritt et al., "Design Principles, Biomedical Data and Clinical Experience with a Polycentric Knee Offering Controlled Stance Phase Knee Flexion: A Preliminary Report", Journal of Prosthetics and Orthotics, vol. 9, No. 1, Winter 1997, pp. 18-24.
Bortz, "A New Mathematical Formulation for Strapdown Inertial Navigation," IEEE Transactions of Aerospace and Electronic Systems, vol. AES-7, No. 1, Jan. 1971.
Bouten et al., "A Triaxial Accelerometer and Portable Data Processing Unit for the Assessment of Daily Physical Activity," IEEE Transactions on Biomedical Engineering, vol. 44, No. 3, Mar. 1997, pp. 136-147.
Bouten et al., "Assessment of Energy Expenditure for Physical Activity Using a Triaxial Accelerometer," Medicine and Science in Sports and Exercise, vol. 26, No. 12, Aug. 1994, pp. 1516-1523.
"C-Leg Fitting Statistics," Abstract, Otto Bock Orthopädische Industrie GMBH & Co., Mar. 2000, pp. 4.
Carlson et al., "Smart Prosthetics Based on Magnetorheological Fluids," 8th Annual Symposium on Smart Structures and Materials, Newport Beach, CA, Mar. 2001, pp. 9.
Carlson, J. David; "What makes a Good MR Fluid?" 8th International Conference on Electrorheological (ER) Fluids and magnetorheological (MR) Suspensions, Nice, Jul. 9-13, 2001, pp. 7.
Claiborne Jr., C.J., "Making Inodes Behave,", Linux Journal, Publ. by SSC Inc, USA, Feb. 2001, No. 82, pp. 94-99.
Copes Inc., "Copes/Bionic Ankle," The Most Significant Development in Ankle Prosthetics in Over a Half Century, Brochure, Nov. 1985, pp. 3.
Crago et al., "New Control Strategies for Neuroprosthetic Systems," Journal of Rehabilitation Research and Development, vol. 33, No. 2, Apr. 1996, pp. 158-172.
Dai et al., "Application of Tilt Sensors in Functional Electrical Stimulation," IEEE Transactions on Rehabilitation Engineering, vol. 4, No. 2, Jun. 1996, pp. 63-72.
Dietl et al., "Der Einsatz von Elektronik bei Prothesen zur Versorgung der unteren Extremität," Med. Orth. Tech., 1997, vol. 117, pp. 31-35.
Elliott, Scott B.; "MR Microprocessor-Controlled Swing and Stance," Presentation to American Academy of Orthotists & Prosthetists (Feb. 4, 2004), 81 pages.

Fisekovic et al., "New Controller for Functional Electrical Stimulation Systems," Medical Engineering & Physics, vol. 23, 2001, pp. 391-399.
Flowers et al., "An Electrohydraulic Knee-Torque Controller for a Prosthesis Simulator," Journal of Biomechanical Engineering: Transactions of the ASME; vol. 99, Series K, No. 1; Feb. 1977, pp. 3-8.
Foerster et al., "Detection of Posture and Motion by Accelerometry: A Validation Study in Ambulatory Monitoring," Computers in Human Behavior, vol. 15, 1999, pp. 571-583.
Foxlin et al., "Miniature 6-DOF Inertial System for Tracking HMDs," SPIE, vol. 3362, Apr. 13-14, 1998, pp. 15.
Frank et al., "Reliable Real-Time Recognition of Motion Related Human Activities Using MEMS Inertial Sensors," 2010, pp. 14, http://www.xsens.com/imagesjstories/PDF/Activity_Recognition_Final_ION_2010_Paper.pdf.
Fujita et al., "Joint Angle Control with Command Filter for Human Ankle Movement Using Functional Electrical Stimulation," Proceedings of the 9th Annual Conference of the IEEE Engineering in Medicine and Biology Society, Nov. 13-16, 1987, Ch. 2513, vol. 3, pp. 1719-1720.
Gélat et al., "Adaptation of the Gait Initiation Process for Stepping on to a New Level Using a Single Step," Experimental Brain Research, vol. 133, Jun. 2000, pp. 538-546.
Graps, Amara; "An Introduction to Wavelets," IEEE Computational Science & Engineering, vol. 2, No. 2, Summer 1995, pp. 50-61.
Grimes, Donald L., "An Active Multi-Mode Above-Knee Prosthesis Controller," Massachusetts Institute of Technology, Thesis, Jun. 1979, in 158 pages.
Grönqvist et al., "Human-Centered Approaches in Slipperiness Measurement," NIH Public Access, Author Manuscript, 2001, pp. 32. http://www.ncbi.nlm.nih.gov/pmc/articles/PMC2895265/.
Hanafusa et al., "A Robot Hand with Elastic Fingers and Its Application to Assembly Process," Robot Motion, Brady et al., MIT Press, Cambridge, MA, 1982, pp. 337-359.
Hanson et al., "Predicting Slips and Falls Considering Required and Available Friction," Ergonomics, vol. 42, No. 12, 1999, pp. 1619-1633.
Hashimoto et al., "An Instrumented Compliant Wrist Using a Parallel Mechanism," Japan/USA Symposium on Flexible Automation, vol. 1, ASME, 1992, pp. 741-744.
Hayes et al., "Leg Motion Analysis During Gait by Multiaxial Accelerometry: Theoretical Foundations and Preliminary Validations," Journal of Biomechanical Engineering, vol. 105, Aug. 1983, pp. 283-289.
Herr et al., "User-Adaptive Control of a Magnetorheological Prosthetic Knee," Industrial Robot: An International Journal, vol. 30, No. 1, 2003. pp. 42-55.
Herr, Hugh; "Experiencing the Frontiers of Biomedical Technology," Presentation, Harvard—MIT Division of Health Sciences & Technology, Mar. 10-11, 2003, Harvard Medical School, p. 1.
Herr et al., "Patient-Adaptive Prosthetic and Orthotic Leg Systems," In Proceedings of the 12th Nordic Baltic Conference on Biomedical Engineering and Medical Physics, Jun. 18-22, 2002, pp. 18-21.
Heyn et al., "The Kinematics of the Swing Phase Obtained From Accelerometer and Gyroscope Measurements," 18th Annual International Conference of the IEEE Engineering in Medicine and Biology Society, Amsterdam 1996, pp. 463-464.
Hill et al., "Altered Kinetic Strategy for the Control of Swing Limb Elevation Over Obstacles in Unilateral Below-Knee Amputee Gait," Journal of Biomechanics, vol. 32, 1999, pp. 545-549.
Howard, Russell Duane; "Joint and Actuator Design for Enhanced Stability in Robotic Force Control," Massachusetts Institute of Technology, Thesis, Sep. 1990 (believed to be catalogued on or after Sep. 19, 1990) in 219 pages.
Jones et al., The gait initiation process in unilateral lower-limb amputees when stepping up and stepping down to a new level, Clinical Biomechanics, 2005, vol. 20, pp. 405-413 (9 pages).
Jonic et al., "Three Machine Learning Techniques for Automatic Determination of Rules to Control Locomotion," IEEE, Transactions on Biomedical Engineering, vol. 46, No. 3, Mar. 1999, pp. 300-310.

(56) References Cited

OTHER PUBLICATIONS

Kidder et al., "A System for the Analysis of Foot and Ankle Kinematics During Gait," IEEE Transactions on Rehabilitation Engineering, vol. 4, No. 1, Mar. 1996, pp. 25-32.

Kirkwood et al., "Automatic Detection of Gait Events: A Case Study Using Inductive Learning Techniques," Journal of Biomedical Engineering, vol. 11, Nov. 1989, pp. 511-516.

Kirsner, Scott; "A Step in the Right Direction Biomedical Horizons Expanding," Boston Globe, Mar. 17, 2003, pp. 4.

Kostov et al., "Machine Learning in Control of Functional Electrical Stimulation Systems for Locomotion," IEEE Transactions on Biomedical Engineering, vol. 42, No. 6, Jun. 1995, pp. 541-551.

Kuster et al., "Kinematic and Kinetic Comparison of Downhill and Level Walking," Clinical Biomechanics, vol. 10, No. 2, 1995, pp. 79-84.

LeFebvre, W., "Permissions and Access Control Lists", UNIX Review's Performance Computing, Publ. by Miller Freeman, USA, Oct. 1998, vol. 16, No. 11, pp. 59-61.

LaFortune, Mario A.; "Three Dimensional Acceleration of the Tibia During Walking and Running," Journal of Biomechanics, vol. 24, No. 10, 1991, pp. 877-886.

Lee et al., "Activity and Location Recognition Using Wearable Sensors," Pervasive Computing, Jul.-Sep. 2002, pp. 24-32.

Lelas et al., "Hydraulic Versus Magnetorheological-Based Electronic Knee Prostheses: A Clinical Comparison," Massachusetts, 2004, pp. 1-16.

Light et al., Skeletal Transients on Heel Strike in Normal Walking with Different Footwear, Journal of Biomechanics, vol. 13, 1980, pp. 477-480.

Luinge, H.J.; "Inertial Sensing of Human Movement," University of Twente, Netherlands, Thesis, Oct. 30, 2002 in 88 pages.

"MT9 Inertial 3D Motion Tracker," Xsens Technologies B.Y., available at http://www.xsens.com/download/MT9_brochure.pdf (at least as early as Oct. 2004), printed Jul. 20, 2006, 2 pages.

"Magnetic Fluid Improves Mobility of Prostetic Leg", Advanced Materials & Processes, Sep. 2003, vol. 9, Issue 161, pp. 29-30, 3 pages.

Martens, W.L.J.; "Exploring Information Content and Some Application of Body Mounted Piezo-Resistive Accelerometers," In P.H. Veltink, & R.C. van Lummel (Eds.), Dynamic analysis using body fixed sensors, Second World Congress of Biomechanics, Amsterdam, 1994, pp. 9-12.

Mayagoitia et al., "Accelerometer and Rate Gyroscope Measurement of Kinematics: An Inexpensive Alternative to Optical Motion Analysis Systems," Journal of Biomechanics, vol. 35, 2002, pp. 537-542.

Michel et al., "The Strategies to Regulate and to Modulate the Propulsive Forces During Gait Initiation in Lower Limb Amputees", Experimental Brain Research, May 27, 2004, vol. 158, pp. 356-365.

Moe-Nilssen, R.; "A New Method for Evaluating Motor Control in Gait Under Real-Life Environmental Conditions. Part 1: The Instrument" Clinical Biomechanics, vol. 13, 1998, pp. 320-327.

Moe-Nilssen, R.; "A New Method for Evaluating Motor Control in Gait Under Real-Life Environmental Conditions. Part 2: Gait Analysis" Clinical Biomechanics, vol. 13, 1998, pp. 328-335.

Morris, J.R.W.; "Accelerometry—A Technique for the Measurement of Human Body Movements," Journal of Biomechanics, vol. 6, 1973, pp. 729-736.

Moseley et al., "High- and Low-Ankle Flexibility and Motor Task Performance," Gait and Posture, vol. 18, 2003, pp. 73-80.

Murray et al., "Walking Patterns of Normal Men," The Journal of Bone and Joint Surgery, vol. 46-A, No. 2, Mar. 1964.

Nadeau et al., "Frontal and Sagittal Plane Analyses of the Stair Climbing Task in Healthy Adults Aged Over 40 Years: What are the Challenges Compared to Level Walking?" Clinical Biomechanics, vol. 18, 2003, pp. 950-959.

Nakagawa, Akio; "Intelligent Knee Mechanism and the Possibility to Apply the Principle to the Other Joints," Proceedings of the 20th Annual International Conference of the IEEE Engineering in Medicine and Biology Society, vol. 20, No. 5, Dec. 1998, pp. 2282-2287.

Namespaces in XML, World Wide Web Consortium Working Draft Sep. 16, 1998; Tim bray (Textuality); Dave Hollander (Hewlett-Packard Company); Andrew Layman (Microsoft).

Ossur Academy, 2004 Course Descriptions, OSSUR North America, 16 pages.

Otto Bock®, "C-LEG: A New Dimension in Amputee Mobility," Otto Bock Data Sheet, Otto Bock Orthopadische Industrie, 1997, pp. 4.

"The Electronic C-Leg® Compact Leg Prosthesis System," Instructions for Use, Otto Bock®, Otto Bock Healthcare Products GmbH, 2002, pp. 28.

Otto Bock's C-Leg, see http://web.archive.org/web/20040215152410/http:/www.ottobockus.com/products/lower_limb_prosthetics/c-leg.asp Asserted by iWalk in Civil Action No. 12-CV-11061 FDS as known or used in this country before Jul. 15, 2004 and on sale in this country more than one year before Jul. 15, 2004.

"The Electronic C-Leg® Knee Joint System," Instructions for Use, Otto Bock®, 2002, pp. 30. http://www.ottobockus.com/products/lower_limb_prosthetics/c-leg_instructions.pdf (printed Jul. 20, 2006).

Otto Bock, Quality for Life, Software C-Soft, Menu-driven setting of the C-Leg, 2004 1 page.

Otto, Judith, "Prosthetic Knees: What's on the Way?" The O&P edge, http://www.oandp.com/edge/issues/articles/2003-10_02.asp, Oct. 2003, 5 pages.

Otto, Judith, "Prosthetic Knees: What's Currently New and Impressive?" The O&P Edge, http://www.oandp.com/edge/issues/articles/2003-10_03.asp, Oct. 2003, 4 pages.

Perry, Jacquelin MD, "Gait Analysis:Normal and Pathological Function," Ch. 4, pp. 51-53, 85-87, 1992.

Petrofsky et al., "Feedback Control System for Walking in Man," Computers in Biology and Medicine, vol. 14, No. 2, pp. 135-149, 1984.

Pfeffer et al., "Experiments with a Dual-Armed, Cooperative, Flexible-Drivetrain Robot System," Proceedings of 1993 IEEE International Conference on Robotics and Automation, vol. 3, May 5, 1993, pp. 601-608.

Popovic et al., "Control Aspects of Active Above-Knee Prosthesis," International Journal of Man-Machine Studies, vol. 35, No. 6, Dec. 1991, pp. 751-767.

Popovic et al., "Optimal Control for an Above-Knee Prosthesis With Two Degrees of Freedom," Journal of Biomechanics, vol. 28, No. 1, 1995, pp. 89-98.

Powers et al., Stair Ambulation in Persons with Transtibial Amputation: An Analysis of the Seattle LightFoot™, Journal of Rehabilitation Research and Development, vol. 34, No. 1, Jan. 1997, pp. 9-18.

Proteor, "Assembly and Adjustment Instructions for IP50-R," Sep. 2004, pp. 1-21.

Rao et al., "Segment Velocities in Normal and Transtibial Amputees: Prosthetic Design Implications," IEEE Transactions on Rehabilitation Engineering, vol. 6, No. 2, Jun. 1998, pp. 219-226.

Redfern et al., "Biomechanics of Descending Ramps," Gait and Posture, vol. 6, 1997, pp. 119-125.

Reitman et al., "Gait Analysis in Prosthetics: Opinions, Ideas, and Conclusions," Prosthetics and Orthotics International, vol. 26, 2002, 50-57.

Riener et al., "Stair Ascent and Descent at Different Inclinations," Gait and Posture, vol. 15, 2002, pp. 32-44.

Robinson, David William; "Design and Analysis of Series Elasticity in Closed-Loop Actuator Force Control," Massachusetts Institute of Technology, Thesis, Jun. 2000 in 123 pages.

Robinson et al., "Series Elastic Actuator Development for a Biomimetic Walking Robot," MIT Leg Laboratory, 1999, pp. 1-8.

Schmalz et al., "Energy Efficiency of Trans-Femoral Amputees Walking on Computer-Controlled Prosthetic Knee Joint 'C-Leg,'" International Society for Prosthetics and Orthotics: Conference Book 9th World ISPO—World Congress, 1998, pp. 3.

(56) References Cited

OTHER PUBLICATIONS

Sekine et al., "Classification of Waist-Acceleration Signals in a Continuous Walking Record," Medical Engineering & Physics, 2000, pp. 285-291.
Sin et al., "Significance of Non-Level Walking on Transtibial Prosthesis Fitting with Particular Reference to the Effects of Anterior-Posterior Alignment," Journal of Rehabilitation Research and Development, vol. 38, No. 1, Jan./Feb. 2001, pp. 1-6.
Smidt et al., "An Automated Accelerometry System for Gait Analysis," Journal of Biomechanics, vol. 10, 1977, pp. 367-375.
"State-of-the-Art Prosthetic Leg Incorporates Magneto-Rheological Technology," Medical Product Manufacturing News, Nov. 2000, p. 42 [Web version attached in 3 pages].
Suga et al., "Newly Designed Computer Controlled Knee-Ankle-Foot Orthosis (Intelligent Orthosis)", Prosthetics and Orthotics International, vol. 22, 1998, pp. 230-239.
Sugano et al., "Force Control of the Robot Finger Joint Equipped with Mechanical Compliance Adjuster," Proceedings of the 1992 IEEE/RSJ International Conference on Intelligent Robots & Systems, Jul. 7-10, 1992, pp. 2005-2013.
Thakkar, Sneha, "Energy Economy Gait Analysis of an Autoadaptive Prosthetic Knee," Massachusetts Institute of Technology, Thesis, Aug. 30, 2002 in 58 pages.
Tomović et al., "A Finite State Approach to the Synthesis of Bioengineering Control Systems," IEEE Transactions of Human Factors in Electronics, vol. HFE-7, No. 2, Jun. 1966, pp. 65-69.
Tong et al., "A Practical Gait Analysis System Using Gyroscopes," Medical Engineering and Physics, vol. 21, 1999, pp. 87-94.
Tong et al., "Virtual Artificial Sensor Technique for Functional Electrical Stimulation," Medical Engineering & Physics, vol. 20, 1998, pp. 458-468.
Townsend et al., "Biomechanics and Modeling of Bipedal Climbing and Descending," Journal of Biomechanics, vol. 9, No. 4, 1976, pp. 227-239.
Van Den Bogert et al., "A Method for Inverse Dynamic Analysis Using Accelerometry," Journal of Biomechanics, vol. 29, No. 7, 1996, pp. 949-954.
Van Der Kooij et al., "A Multisensory Integration Model of Human Stance Control," Biological Cybernetics, vol. 80, pp. 299-308, 1998.
Van Der Loos et al., "ProVAR Assistive Robot System Architecture," Proceedings of the 1999 IEEE International Conference on Robotics & Automation, Detroit, Michigan, vol. 1, May 1999, pp. 741-746.
Veltink et al., "Detection of Static and Dynamic Activities using Uniaxial Accelerometers," IEEE Transactions on Rehabilitation Engineering, vol. 4, No. 4, Dec. 1996, pp. 375-385.
Veltink et al., "The Feasibility of Posture and Movement Detection by Accelerometry," 15th Annual International Conference of the IEEE Engineering in Medicine and Biology Society, Oct. 28-31, 1993, San Diego, California, pp. 1230-1231.
Wilkenfeld, Ari J, Ph.D.; "An Auto-Adaptive External Knee Prosthesis," Artificial Intelligence Laboratory, MIT, Sep. 2000, pp. 3.
Wilkenfeld, Ari J, Ph.D.; "Biologically Inspired Autoadaptive Control of a Knee Prosthesis," Massachusetts Institute of Technology, Thesis, Jul. 2000, (believed to be catalogued on or after Oct. 23, 2000) in 106 pages.
Willemsen et al., "Automatic Stance-Swing Phase Detection from Accelerometer Data for Peroneal Nerve Stimulation," IEEE Transactions on Biomedical Engineering, vol. 37, No. 12, Dec. 1990, pp. 1201-1208.
Willemsen et al., "Real-Time Gait Assessment Utilizing a New Way of Accelerometry," Journal of Biomechanics, vol. 23, No. 8, 1990. pp. 859-863.
Williamson, Matthew M.; "Series Elastic Actuators," Massachusetts Institute of Technology Artificial Intelligence Laboratory, A.I. Technical Report No. 1524, Jan. 1995, pp. 1-83.
Woodward et al., "Skeletal Accelerations Measured During Different Exercises," Proceedings of the Institution of Mechanical Engineers, Part H, Journal of Engineering in Medicine, vol. 207, No. 2, Jun. 1993, pp. 79-85.
Wu et al., "The Study of Kinematic Transients in Locomotion Using the Integrated Kinematic Sensor," IEEE Transactions on Rehabilitation Engineering, vol. 4, No. 3, Sep. 1996, pp. 193-200.
Zamiska, Nicholas, "Bionic Knee 'Learns' How to Walk", The Wall Street Journal, Jul. 6, 2004, pp. 1.
Complaint for Patent Infringement filed Nov. 15, 2011, Össur hf v. iWalk, Inc. (involving U.S. Pat. No. 7,431,737 and 7,896,927), Case No. SACV11-01759 AN, 85 pages.
Defendant iWalk's First Amended Answer and Counterclaim to Plaintiffs' Complaint for Patent Infringement, Ossur v Iwalk, Jan. 26, 2012, 20 pages.
Defendant iWalk's Answer and Counterclaim to Plaintiffs' Complaint for Patent Infringement, Ossur v. iWalk, Jan. 6, 2012, pp. 95.
Defendant's Amended Answer and Counterclaim, filed Feb. 3, 2012, Case No. SACV11-01759 (involving U.S. Pat. No. 7,431,737 and 7,896,927), Össur Hf v. iWalk, Inc., 94 pages.
Defendant's Reply in Support of Its Motion to Transfer Venue, filed Apr. 23, 2012, Case No. SACV11 01759 (involving U.S. Pat. No. 7,431,737 and 7,896,927), Össur Hf v. iWalk, Inc.
Memorandum of Points and Authorities in Support of Defendant's Motion to Transfer Venue, filed Apr. 2, 2012, Case No. SACV11-01759 (involving U.S. Pat. No. 7,431,737 and 7,896,927), Össur Hf v. iWalk, Inc.
Official Communication in European Patent Application No. 06733301.3, dated May 8, 2009 in 6 pages.
Ossur's Reply to iWalk's Amended Counterclaims and Demand for Jury Trial, Ossur v Iwalk, Feb. 9, 2012, 8 pages.

\* cited by examiner

COMBINED ACTIVE AND PASSIVE LEG PROSTHESIS SYSTEM AND A METHOD FOR PERFORMING A MOVEMENT WITH SUCH A SYSTEM

CROSS-REFERENCE TO RELATED APPLICATIONS

This application is a continuation application of U.S. patent application Ser. No. 13/846,695, entitled COMBINED ACTIVE AND PASSIVE LEG PROSTHESIS SYSTEM AND A METHOD FOR PERFORMING A MOVEMENT WITH SUCH A SYSTEM, and filed Mar. 18, 2013, which is a continuation application of U.S. patent application Ser. No. 11/887,374, entitled COMBINED ACTIVE AND PASSIVE LEG PROSTHESIS SYSTEM AND A METHOD FOR PERFORMING A MOVEMENT WITH SUCH A SYSTEM, and filed Jul. 30, 2009, which is a national stage entry of International Patent Application No. PCT/SE2006/000445, entitled COMBINED ACTIVE AND PASSIVE LEG PROSTHESIS SYSTEM AND A METHOD FOR PERFORMING A MOVEMENT WITH SUCH A SYSTEM, and filed Apr. 18, 2006, the entireties of which are incorporated by reference herein and should be considered a part of this specification.

BACKGROUND

Field

The present invention relates generally to a method for a combined active and passive leg prosthesis system and a combined active and passive leg prosthesis system for replacing a missing lower extremity of an individual to perform a gait cycle (take a step) by the leg prosthesis system. The leg prosthesis system has at least one movable joint and a drive unit to drive the movable joint.

More specifically, the present invention concerns a leg prosthesis system intended for a person who has a leg amputated above or below the knee joint. Thus the system may comprise an articulated ankle joint or both an articulated knee joint and an articulated ankle joint.

Description of the Related Art

A leg prosthesis system of the type stated above can be adjusted and used by wearers of a prosthesis at different amputation levels.

A person uses his entire body to perform a movement. A gait cycle, that is two steps, is divided into a support phase and a swing phase. The support phase is when the foot of the leg is in contact with the ground, and during the swing phase the foot swings freely in the air. In walking, one leg swings forward with a flexion in hip, knee and ankle joint while at the same time the arm on the opposite side swings forward. The arm on the same side swings backward and helps to increase the forward force and promotes balance. When the foot of the leg touches the ground, heel touching ground, the weight of the body is supported and the forward fall is braked. The leg supports the body and drives it forward until the next leg takes over in placing the heel on the ground.

If one or more joints and muscles are missing, in this case in lower extremities, there will be imbalance and more energy will be consumed. The more joints that are missing and the higher the amputation level, the more energy is required to perform a gait cycle.

A gait cycle, in this case for a leg prosthesis system, can be identified as the movement performed by leg prosthesis system from placing the heel on the ground to the next placing of the heel on the ground with the same leg.

A leg prosthesis system according to the invention can be used to facilitate different types of gait cycles for the prosthesis wearer, for instance to walk at varying speeds, to climb or descend stairs or walk on inclined surfaces.

With the leg prostheses that are available on the market, it is difficult or even impossible for a leg prosthesis wearer to perform certain types of gait cycles.

The leg prosthesis systems that are being sold today are completely passive, that is no external energy is supplied to the prosthesis in addition to the prosthesis wearer's kinetic energy. A passive prosthesis can only lock, dampen and decelerate a movement. With a good passive leg prosthesis system according to prior art technique, a prosthesis wearer can handle most everyday situations, such as sit down, stand, walk on flat ground and descend stairs and slopes.

However, the energy that can be supplied to a passive leg prosthesis system by the prosthesis wearer is in most cases not sufficient to perform more energy-consuming gait cycles, such as stand up from a sitting position, quick increase of speed or climb a staircase or a steep slope. Another problem is to ensure ground clearance to reduce the risk of stumbling.

The manufacture and development of active leg prosthesis systems has only started recently, that is prostheses comprising motors and power sources. By supply of power, the leg prosthesis system helps the prosthesis wearer to perform certain gait cycles such as climb a staircase.

The technique chosen to supply power in active leg prosthesis systems, according to prior art technique, has resulted in problems, such as high movement of inertia in moving the movable joints of the leg prosthesis system. All parts have to be driven when performing a gait cycle and the energy consumption in the leg prosthesis system will be high.

There is thus a need to improve prior art and many of the leg prostheses that are currently available on the market.

SUMMARY

An object of the present invention is to provide a leg prosthesis system which eliminates one of the problems described above in a simple and effective manner.

Another object of the invention is to provide a method of performing gait cycles with improved performance by means of a leg prosthesis.

The above objects and other objects that will be evident from the following description are achieved by a device and a method according to the claims.

A leg prosthesis system according to the invention comprises at least one movable joint which can be switched between being actively driven or being passively braked. Furthermore the leg prosthesis system comprises a control system for controlling the active and the passive unit in the movable joint. A number of transducers and sensors arranged on the leg prosthesis system supply input data to the control system, and a power source supplies power to control system, motors and transducers.

A leg prosthesis system according to the invention comprising control system, power source and transducers can be provided with an ankle joint comprising an active and a passive unit and/or a knee joint comprising an active and a passive unit.

The leg prosthesis system according to the invention can also be adjusted to a prosthesis wearer who lacks both lower extremities, that is who is double-leg-amputated. Each leg prosthesis system may, but need not, comprise one common or two separate or communicating control systems.

According to one aspect of the present invention, a combined active and passive leg prosthesis system is provided to replace a missing lower extremity of an individual to perform a gait cycle by means of the leg prosthesis system. The leg prosthesis system comprises at least one movable joint and an active drive unit to supply power and drive the movable joint. Moreover the active drive unit is disconnectable from driving relation with the movable joint. By the active drive unit being disconnectable, low moment of inertia can be achieved in the movable joint. The forward force in the natural swinging motion created by the wearer's body is then sufficient to move the joint. When the joint is disconnected from driving, it is possible to brake the movement of the joint when required. Braking of the movable joint performed by a passive brake unit may be varied in braking force and be varied from a completely unbraked (freely swinging) to a fully braked (locked) joint. The interaction between active driving and passive braking of a joint gives a prosthesis wearer a good possibility of performing gait cycles with improved performance. An active drive unit which can be run in two directions makes it possible to perform a movement in both directions of the joint if, in addition, it is possible to disconnect the active drive so as to perform a free movement of the joint which can be controlled by the passive brake unit. Active and passive movements are a natural part of the gait pattern, which means that a system having such possibilities can more easily imitate the energy-saving way of the human body to perform movements.

Preferably, the active drive unit of the leg prosthesis system is disconnected from driving relation with the movable joint during part of the gait cycle. For instance, the active drive unit can be disconnected during both the swing and the support phase.

Preferably, a passive brake unit acts on the movement of the joint when the active drive unit is disconnected from the joint. By using the passive brake unit when the active drive unit is disconnected, the energy-saving way of the human body to perform movements can be imitated.

Preferably, the leg prosthesis system according to the invention also comprises a control system adapted to control the active drive unit of the movable joint. The control system makes it possible to control direction, force and speed of the active drive unit. The control system also makes it possible to activate driving only at points of time when the leg prosthesis system needs supply of extra power.

Preferably, the control system according to the invention is also adapted to control the passive brake unit of the movable joint. A control system can be used to adjust the brake force from a completely unbraked (freely swinging) to a fully braked (locked) joint. If the control system controls both the active drive unit and the passive brake unit, a number of advantages can be achieved since the leg prosthesis system according to the invention can use the properties of both the active drive unit and the passive brake unit and also the possibility of switching between driving and braking the movable joint.

Preferably the leg prosthesis system comprises both a movable knee joint and a movable ankle joint. A prosthesis wearer who lacks a knee joint, that is who is amputated above the knee joint, needs a leg prosthesis which has both knee joint and ankle joint. A prosthesis wearer who lacks both lower extremities, that is who is double-leg-amputated, needs a leg prosthesis system with at least two movable joints.

Preferably, the knee joint and the ankle joint are each arranged with a disconnectable active drive unit and a passive brake unit as well as a common control system to control the movements of knee joint and ankle joint in a synchronized manner. In double amputation, two separate or communicating control systems may, but need not, be used. A leg prosthesis system which is made up in this manner can use active and passive techniques for both knee joint and ankle joint. When besides a control system coordinates the movement of the knee joint and the ankle joint, considerable improvements can be achieved compared with a completely passive prosthesis, but also compared with an active prosthesis which comprises a knee joint or a knee joint and an ankle joint which are active but not coordinated with a common control system.

Preferably the leg prosthesis system according to the invention comprises transducers for input data to the control system. Input data can be sent to the system from, for instance, a key set, transducers, sensors (speed, position, angle, pressure), nerve sensors etc.

Preferably, the knee joint and the ankle joint move by switching between the associated active drive unit and passive brake unit during a gait cycle.

A leg prosthesis system according to the invention with a movable knee joint and ankle joint which controls the direction, force and speed of the current control system for the active drive unit and the brake force for the passive brake unit in each joint independently of the other joint thus ensures an optimized and coordinated movement of the leg prosthesis system.

The control system may use information from the entire leg prosthesis system, for instance information from the knee joint when the ankle joint is to be controlled and vice versa.

According to one aspect of the present invention, a method is provided for performing a gait cycle with a combined active and passive leg prosthesis system, which replaces a lacking lower extremity of an individual. The leg prosthesis system comprises at least one movable joint and an active drive unit which supplies power and drives the movable joint. Moreover, the active drive unit is disconnected from driving relation with the movable joint during part of the gait cycle. By disconnecting the drive unit, it is, for instance, possible to use the natural swinging movement during the swing phase in walking. Thus the drive unit need not be adjusted to accomplish movements equivalent to free swinging. The active drive unit can instead be optimized for driving, and energy saving can be ensured since the drive unit is not activated during the entire time of use of the prosthesis.

Preferably the method comprises braking the movement of the joint, with a passive brake unit of the leg prosthesis system according to the invention, when the active drive unit is disconnected from the joint. When the active drive unit is disconnected and the passive brake unit is connected, the prosthesis can move freely by the forward force in the joint in question created by the wearer's body, or the movement of the joint can be braked.

Preferably the method comprises controlling of the drive unit and/or the brake unit of the movable joint by a control system of the leg prosthesis system according to the invention. By using a control system, it is possible to disconnect driving and/or activate the passive brake unit at the correct point of time or taking the outer circumstances into consideration. The braking in the leg prosthesis system is a property which advantageously is coordinated with the driving of the system to achieve a good result.

Preferably the method comprises supplying input data to the control system from transducers of the leg prosthesis system. Input data is sent, for instance, from a key set, transducers, sensors (which record speed, position, angle, pressure), nerve sensors etc.

The method preferably comprises controlling in a synchronized manner the movements of a knee joint and an ankle joint of the leg prosthesis system. The knee joint and the ankle joint each have a disconnectable active drive unit and a passive brake unit as well as a common control system. In a leg prosthesis with both knee joint and ankle joint, improved possibilities are achieved for the prosthesis wearer since a control system which is common to both joints can coordinate the movements of knee joint and ankle joint.

The knee joint and the ankle joint preferably move by switching between the associated drive unit and brake unit during a gait cycle.

Preferably the method comprises controlling, separately or in a communicating manner, the movements of at least two movable joints of leg prosthesis systems adjusted to a double-leg-amputated prosthesis wearer.

The control system may use information from the entire leg prosthesis system, for instance information from the knee joint when the ankle joint is to be controlled and vice versa.

The method preferably comprises driving and braking of knee joint and ankle joint, respectively, during a gait cycle.

BRIEF DESCRIPTION OF THE DRAWINGS

The invention will now be described in more detail with reference to the accompanying drawings, in which.

DETAILED DESCRIPTION

Figure 1:
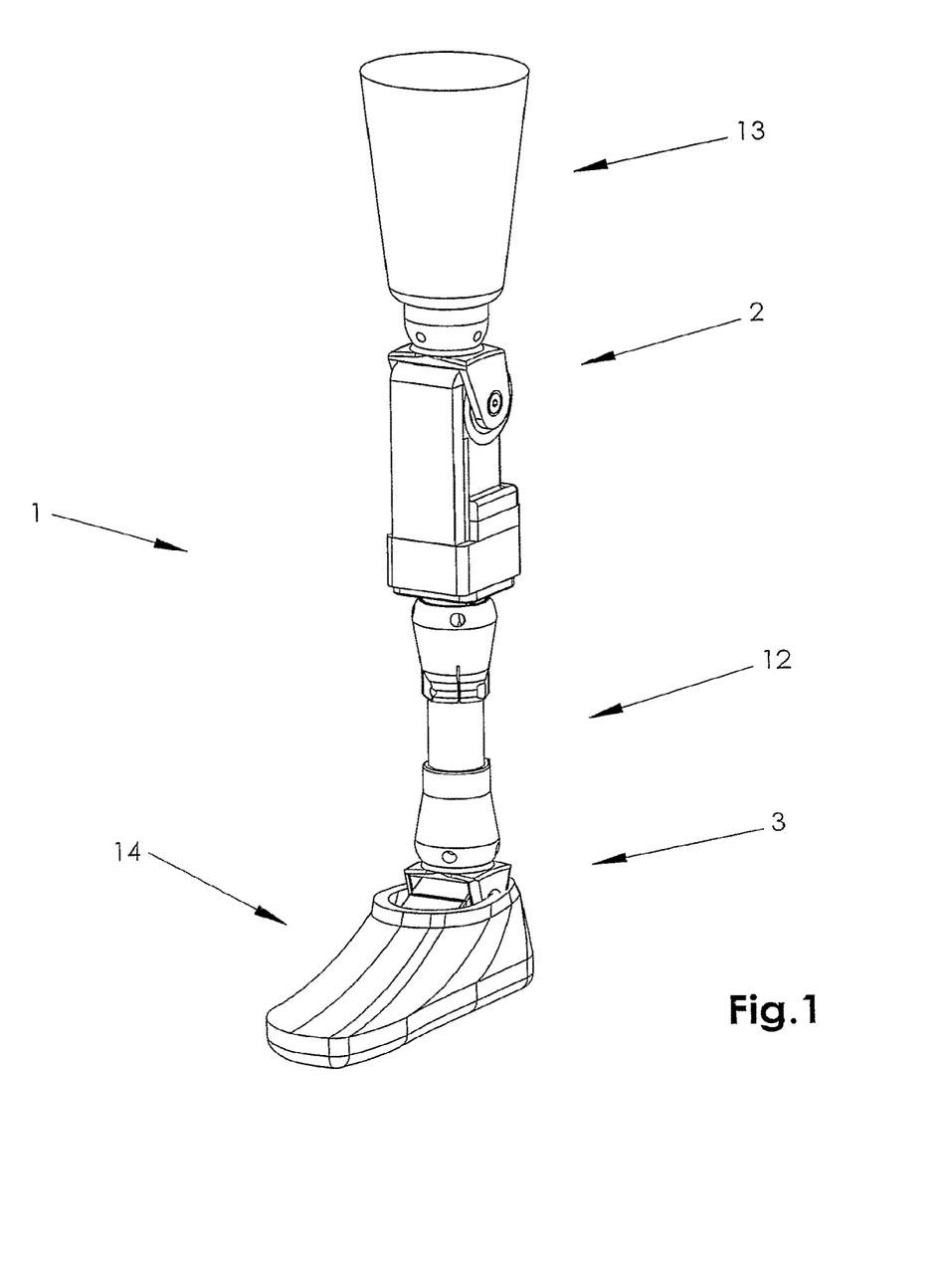
FIG. 1 is a perspective view of a leg prosthesis system according to the invention.

FIG. 1 shows a leg prosthesis system 1 with both knee joint 2 and ankle joint 3 according to the invention and a method of performing a gait cycle with a leg prosthesis system. A prosthesis wearer can attach the prosthesis to the amputated leg by means of the leg-enclosing socket 13. Furthermore the socket 13 is attached to the movable knee joint 2 in a suitable manner and the knee joint is connected to the ankle joint 3 by interconnecting elements 12 or the like. A foot prosthesis 14 is attached to the ankle joint 3 and can turn about the ankle joint 3. Additional components that may be included in a leg prosthesis system are shock absorbers, angularly adjustable couplings etc.

Most of the people with an amputated leg have lost their leg below the knee joint. The present leg prosthesis system and/or method can be used by prosthesis wearers who need a prosthesis with both knee joint and ankle joint, but the invention can also be used for a prosthesis with only an ankle joint or only a knee joint. The leg prosthesis system and/or the method can also be used by prosthesis wearers who lack both lower extremities, that is who are double-leg-amputated and need a leg prosthesis system with at least two movable joints. One common or two separate and/or communicating control means may be used.

Figure 2:
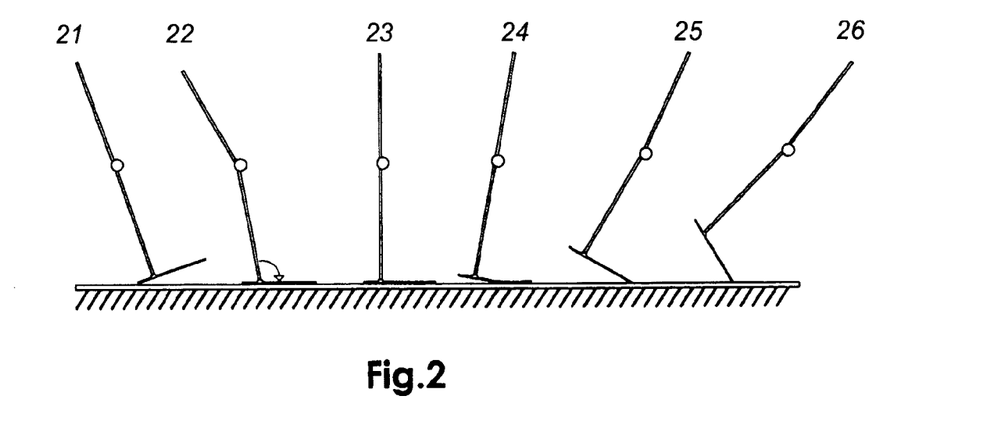
FIG. 2 illustrates the support phase of a gait cycle on a flat surface.

FIG. 2 shows the support phase for a gait cycle on a flat surface. When placing the heel on the surface, 21, the body weight of the prosthesis wearer is applied to the leg prosthesis system. The knee joint then allows flexion and the foot is plantar flexed, 22, that is the foot blade moves away from the lower leg. Body weight and muscular strength help to straighten knee joint and ankle joint to centered standing, 23. In 24, the foot blade is compressed and energy is returned in 25. When performing this movement, from 21 to 25, the leg prosthesis system is completely passive, passive braking of both ankle joint and knee joint. The joints are rotated by means of body weight and muscular strength from the remaining lower extremity. For extra power in the gait, for instance when walking faster, the active drive unit in the foot can be used in the position in 26 to push away.

Figure 3:
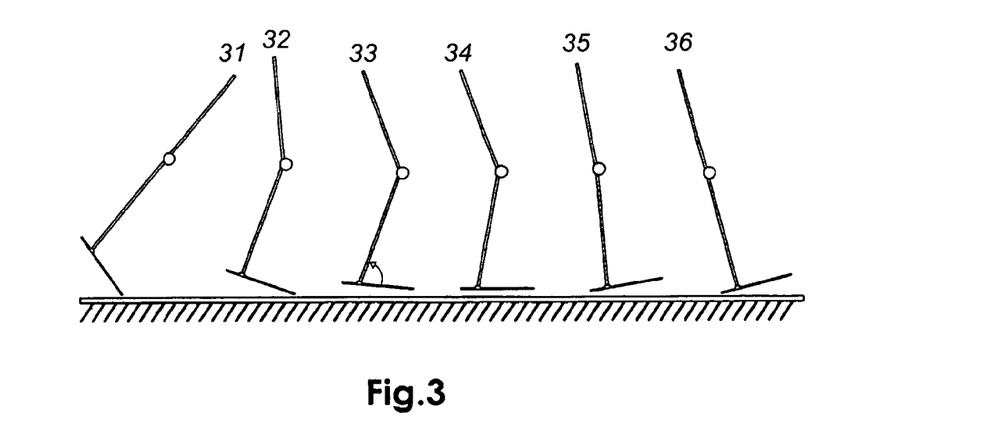
FIG. 3 illustrates the swing phase of a gait cycle on a flat surface.

FIG. 3 shows the swing phase in a gait cycle. 31 corresponds to 26 and when initiating a swing phase, 33, the active part of the ankle joint performs a dorsal flexion, that is the foot blade moves towards the lower leg. This dorsal flexion occurs to give the prosthesis wearer ground clearance, a safe distance between the foot and the ground to prevent stumbling. A passive foot does not manage the dorsal flexion from 32 to 33 but this movement of the foot blade requires some kind of drive. The knee joint performs the swinging movement by using the forward force created by the wearer's body, and the passive braking controls the movement. When performing this movement, from 33 after the dorsal flexion to 35, the leg prosthesis system is completely passive, passive braking of both ankle joint and knee joint. To provide extra force to the step, for instance when walking faster, the active drive unit in the knee joint can be used in the position in 34 to straighten the knee joint and move the lower leg forward more quickly.

To climb a staircase or slope, as illustrated in FIG. 4, FIG. 5, FIG. 7 and FIG. 8, it is important for the knee joint and the ankle joint to cooperate. More energy is required in climbing, which means that cooperating active drive of both ankle joint and knee joint can advantageously help to perform the movement.

Figure 6:
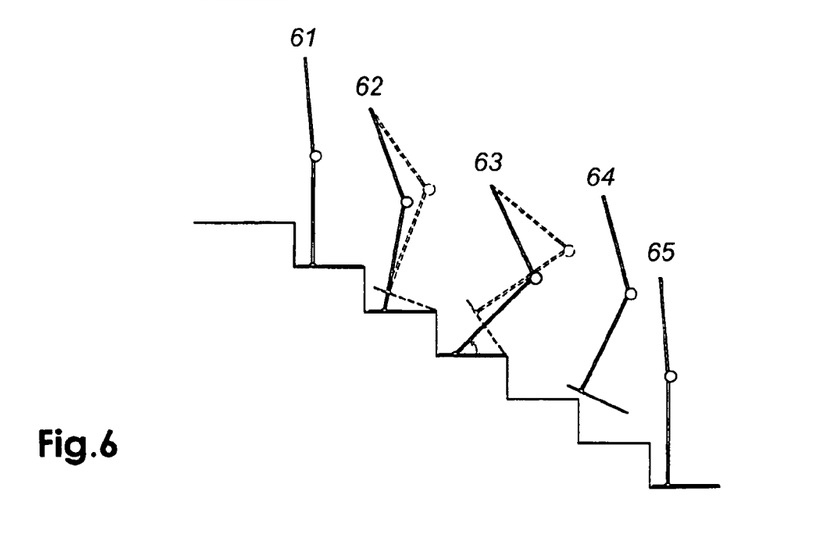
FIG. 6 illustrates the support phase and the swing phase of a gait cycle when descending a staircase.
Figure 9:
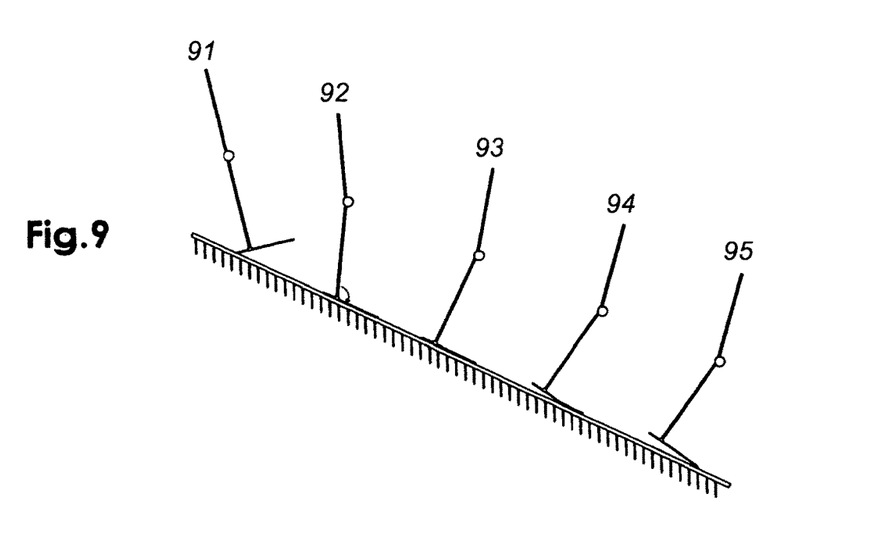
FIG. 9 illustrates the support phase of a gait cycle when descending a slope.

When descending a staircase or slope, as illustrated in FIG. 6 and FIG. 9, the passive braking in both knee joint and ankle joint cooperates.

Figures 4, 5:
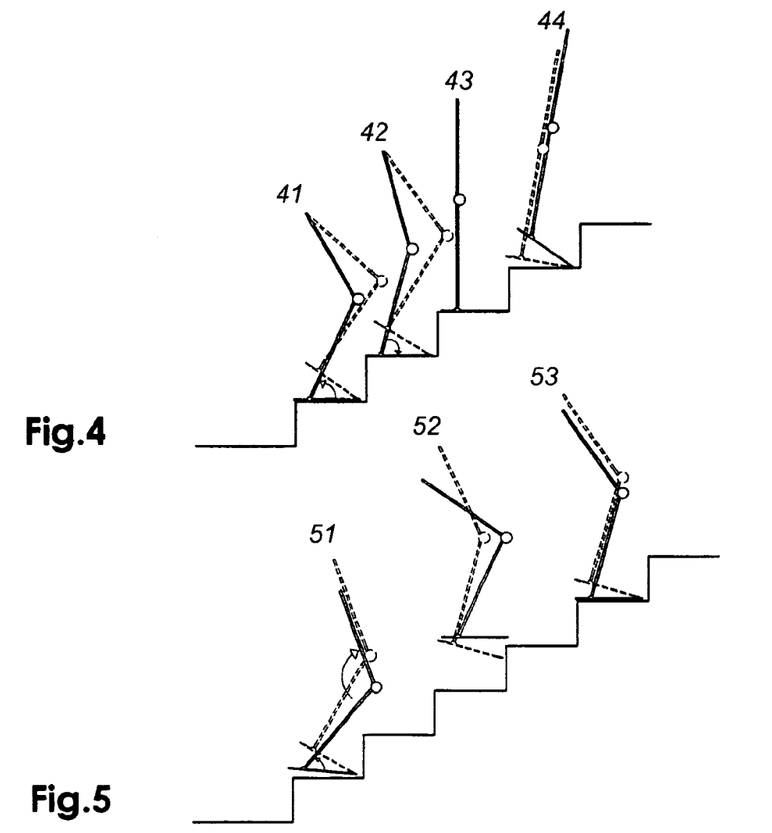
FIG. 4 illustrates the support phase of a gait cycle when climbing a staircase, dashed lines indicating a corresponding gait cycle with a passive/rigid foot.
FIG. 5 illustrates the swing phase of a gait cycle when climbing a staircase.

FIG. 4 to FIG. 6 illustrate the climbing of a staircase. FIG. 4 shows the support phase when climbing a staircase. In 41 the foot is positioned on the step, and balance is achieved. The leg prosthesis system and/or the use of the method according to the invention then push the prosthesis wearer upwards, 42, to centered standing, 43. The control system makes it possible for the knee joint and the ankle joint to cooperate. The active drive unit in the knee joint strives to straighten the knee joint while at the same time the active drive unit in the ankle joint presses the front of the foot towards the ground, 42. In this manner, the ankle joint helps to straighten the knee joint, thereby reducing the energy consumption.

FIG. 4 illustrates the consequences of a passive foot, dashed lines, in combination with an active knee joint. The passive foot gives a higher knee joint position and the gait will be higher than it need be, and it will be more difficult and require more energy for the user to raise himself up on the step. The contact point of the passive foot on the step is moved forwards compared with a foot which can perform a dorsal flexion, which results in also the center of gravity of the body having to be moved forwards. The solid lines indicate how climbing a staircase can be performed using a leg prosthesis according to the invention.

FIG. 5 illustrates the swing phase when climbing a staircase. Also in this case the active drive units in the knee joint and the ankle joint are used. To prevent the prosthesis wearer from hitting the step with his foot and stumbling in the swing phase when climbing a staircase, it is important that the knee joint and ankle joint create a safe distance to the staircase. This is done by the active drive of the knee joint bending the joint and the drive of the ankle joint performing a dorsal flexion of the foot, 51. The leg prosthesis system according to the invention has then created a safe distance to the staircase and also a good starting position for positioning for the next gait. FIG. 5 shows the consequences of a completely passive system, dashed lines. The knee joint does not bend the foot away, and the foot instead bumps into the staircase.

FIG. 6 illustrates the descending of a staircase. Here both knee joint and ankle joint are mainly passive. The movement, 61 to 63, brakes the fall of the body by means of the passive brake units in knee joint and ankle joint. The dashed lines indicate the consequences of a passive foot which is not capable of performing a dorsal flexion. The active drive units can optionally be used to help straighten knee joint and ankle joint in the swing phase.

Figures 7, 8:
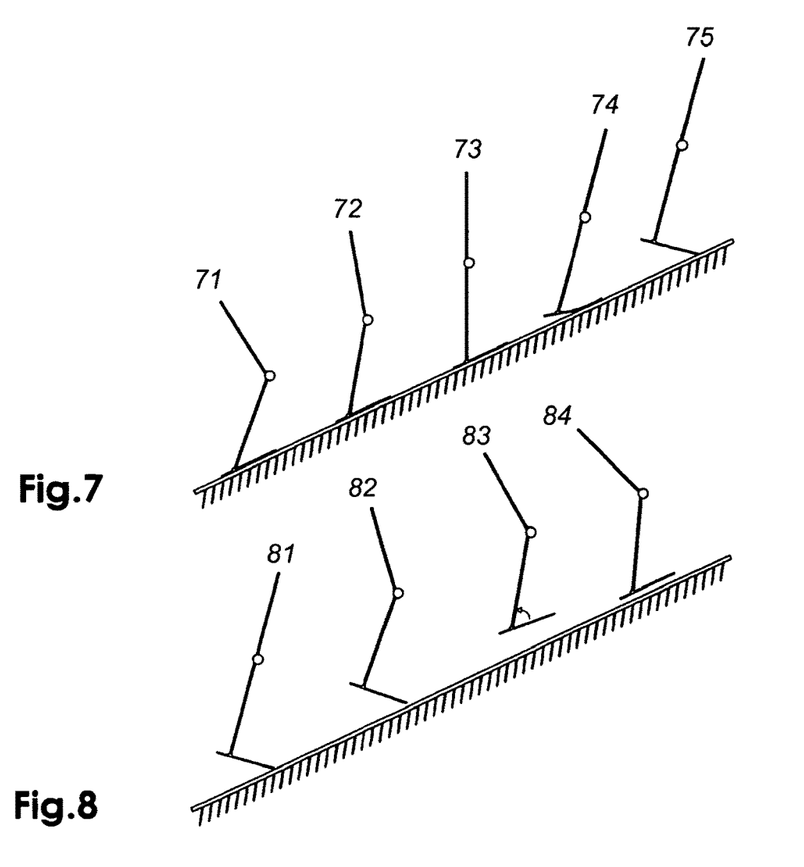
FIG. 7 illustrates the support phase of a gait cycle when climbing a slope.
FIG. 8 illustrates the swing phase of a gait cycle when climbing a slope.

FIG. 7 to FIG. 9 illustrate walking on a very sloping surface. The leg prosthesis system according to the invention then functions in the same way as when climbing a staircase. The angle of knee joint and ankle joint is the only thing that distinguishes the climbing of a staircase from walking on a very sloping surface. When walking on a slightly sloping surface, the walking can be more resembled to walking on flat ground.

FIG. 4, FIG. 5, FIG. 7 and FIG. 8 illustrate ordinary situations which require much energy to be managed. By letting the leg prosthesis system 1 cooperate with the prosthesis wearer's body and existing lower extremities, it is possible to imitate the energy-saving way of the human body to perform the movement. For minimum consumption of energy, all joints in the lower extremities are allowed to cooperate, and the remaining stump of the prosthesis wearer can cooperate with the at least one movable joint in the leg prosthesis system. The leg prosthesis system should supplement the prosthesis wearer and should preferably, but not restrictively, be controlled by him or her.

With a leg prosthesis system 1 and/or a method according to the invention, the disconnectable active drive unit 4, 4' of a knee joint or ankle joint makes it possible for the system and the method to use a combination of active and passive operation. The control system 15 can select the optimal method of performing a movement. The knee joint 2 can be active while the ankle joint 3 is passive and vice versa. For example, the knee joint 2 can perform the swinging movement in the swing phase using only the passive brake unit 5 while the ankle joint 3 uses its active drive unit for dorsal flexion of the foot in order to create extra ground clearance.

Figure 10:
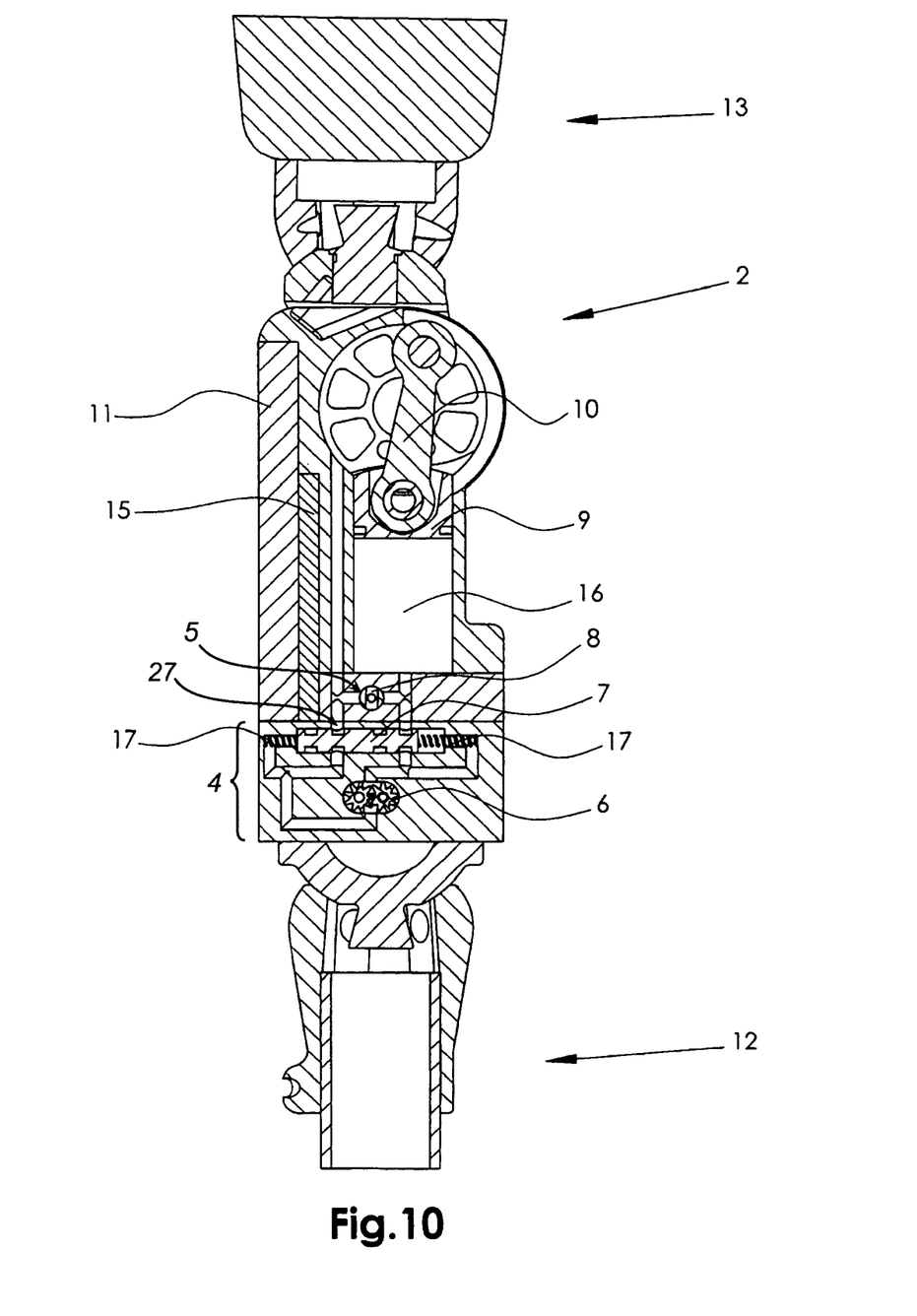
FIG. 10 is a side view in cross-section of a knee in an active straightening position.
Figure 11:
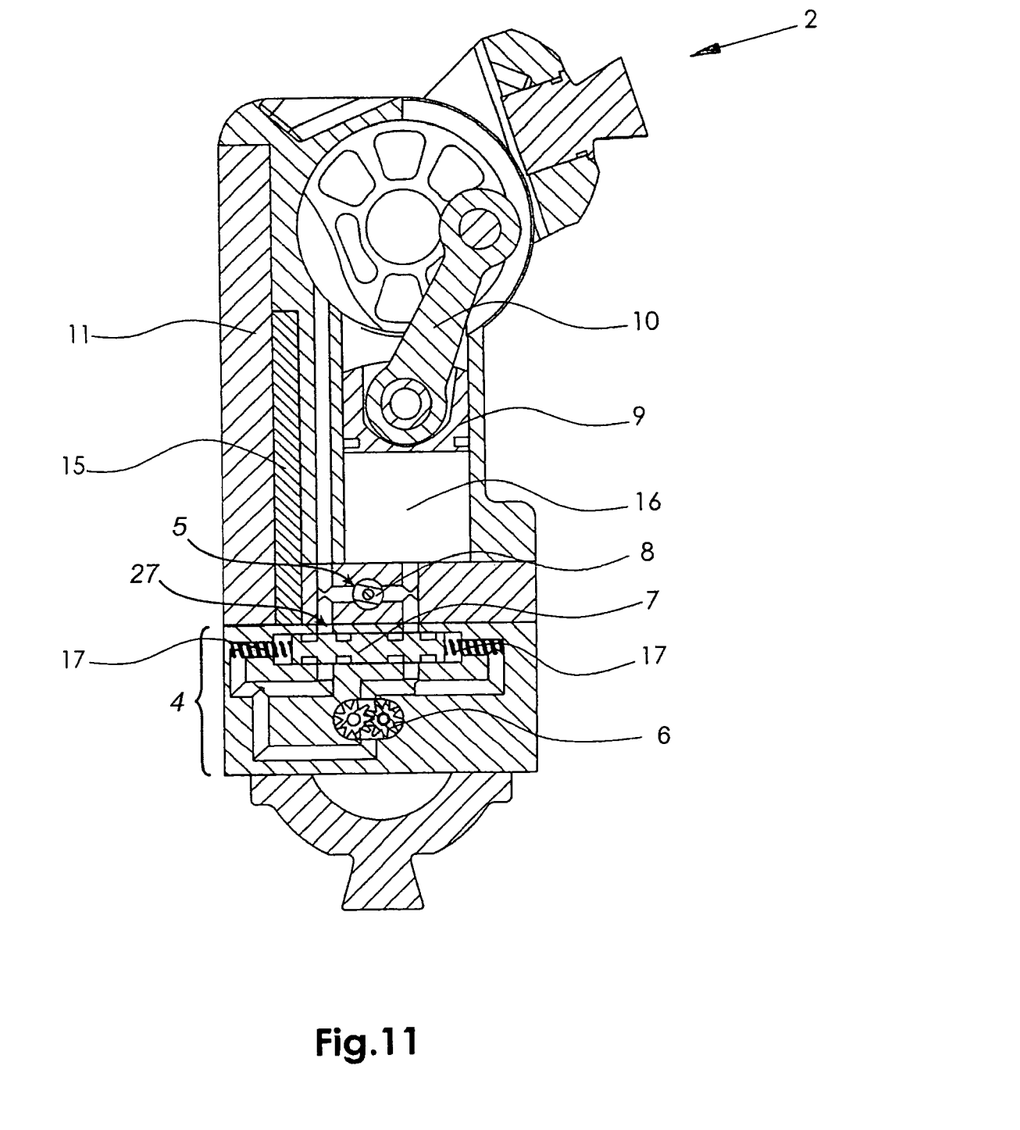
FIG. 11 is a side view in cross-section of a knee in a passive braking position.

FIG. 10 and FIG. 11 are side views in cross-section of a knee joint which, for instance, may be included in the leg prosthesis system 1. The socket 13 is connected to the movable knee joint 2 which in turn is connected to a hydraulic piston 9 via a link arm 10. FIG. 11 shows how the piston 9 is moved when the knee joint is angled. FIG. 10 shows a knee joint 2 according to the invention in its active state with a drive unit 4, a brake unit 5 and a control system 15. In this embodiment, the brake unit 5 involves throttling of the hydraulic oil which provides braking/dampening of the movement of the joint. The battery 11 drives the hydraulic pump 6 of the drive unit 4 via a motor 19 (FIG. 13), and a motor 20 (FIG. 13) for operating the valve 8 of the brake unit 5. The battery 11 also drives the control system 15 and transducers 18a and sensors 18b (FIG. 13) of the leg prosthesis system 1. The control system 15 in turn controls the drive unit 4 and the brake unit 5 and receives input data from transducers and sensors; in addition the control system 15 coordinates the movements of the knee joint 2 and the ankle joint 3.

For activation of the drive unit 4, according to FIG. 10, the hydraulic pump 6 is started, the pressure increases on one side of the pump 6 and, via one of the ducts which open adjacent to the spring 17, the valve cone 7 is pressed aside and the duct system of the drive unit will communicate with the cylinder 16 where the piston 9 works and thus the pump 6 actuates the piston 9 in one or the other direction. When the active drive unit 4 is activated, the valve 8 in the passive brake unit 5 should be completely closed to be able to use the maximum efficiency of the hydraulic pump 6. The active drive unit can drive the knee joint 2 in both directions, in the direction towards a straightened knee joint and in the direction to bend the knee joint. In FIG. 10, the active drive unit acts to straighten the knee joint 2. When the piston 9 is moved in the cylinder 16, it acts on the link arm 10 which in turn acts on the knee joint 2 to perform a movement. Alternative types of driving and motors can be used for the leg prosthesis system other than those mentioned above.

According to FIG. 11 the drive unit 4 is disconnected by the hydraulic pump 6 being switched off. The pressure decreases and the spring 17 presses the valve cone 7 back to its rest position, that is the valve cone 7 closes the ducts to the drive unit 4. Thus, the active drive unit is disconnected from driving relation 27 with the movable joint. The brake unit 5 is activated when the drive unit 4 is disconnected. A movement of the knee joint 2 actuates the piston 9 via the link arm 10, the hydraulic oil in the cylinder 16 is pressed through the valve 8 of the brake unit 5 and the degree of braking/dampening can be adjusted by varying the opening degree of the valve 8. The braking can be varied in brake force and can be varied from a completely unbraked (freely swinging) to a completely braked (locked) knee joint 2.

Figure 12:
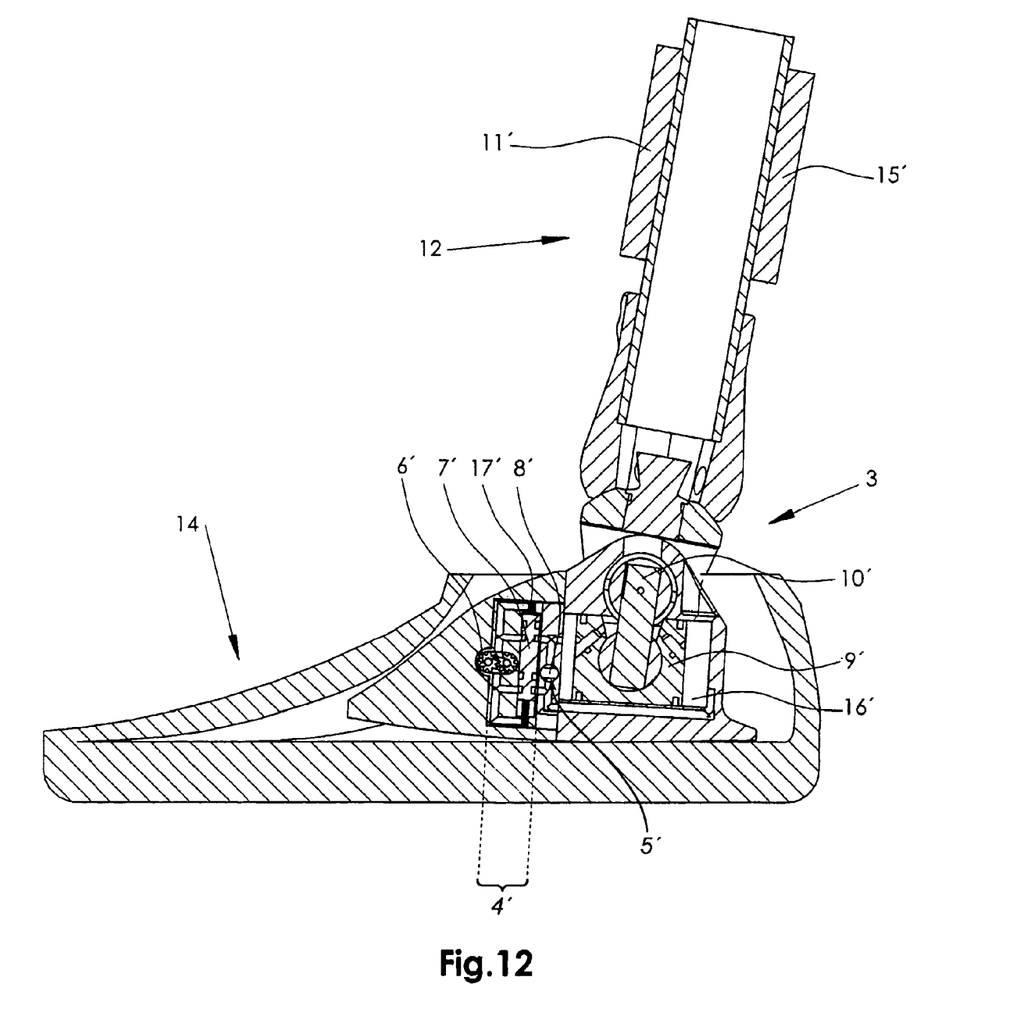
FIG. 12 is a side view in cross-section of a foot in an active position according to the invention.

The foot 14 with the ankle joint 3 according to FIG. 12 is shown in its active state and functions similarly to the knee joint according to FIG. 10 and FIG. 11. To activate the drive unit, the hydraulic pump 6' is started, the pressure is increased on one side of the pump 6' and via one of the ducts which open adjacent to the spring 17', the valve cone 7' is pressed aside and the duct system of the drive unit will communicate with the cylinder 16' where the piston 9' works. In this manner, the pump 6' actuates the piston 9' in one or the other direction. When the active drive unit 4' is activated, the valve 8' in the passive brake unit 5' should be completely closed to be able to use the maximum efficiency of the hydraulic pump 6'. The piston 9' actuates the link arm 10' which in turn actuates the ankle joint 3 to perform a movement of the foot 14 relative to the interconnecting element 12. The drive unit 4' is disconnected by the hydraulic pump 6' being switched off. The pressure decreases and the spring 17' presses the valve cone 7' back to its rest position, that is the valve cone 7' closes the ducts to the drive unit 4'. The brake unit 5' in FIG. 12 is then activated; in normal working conditions the hydraulic pump 6' is then switched off.

A movement of the ankle joint 3 in the passive state actuates the piston 9' via the link arm 10', the hydraulic oil in the cylinder 16' is pressed through the valve 8' of the brake unit 5' and the brake force can be adjusted by varying the opening degree of the valve 8'. The braking can be varied in brake force and can be varied from a completely unbraked (freely swinging) to a fully braked (locked) ankle joint 3.

If the leg prosthesis system 1 merely comprises a foot prosthesis 3 according to the invention, for instance at an amputation level below the knee joint, the foot prosthesis still needs a battery 11' and a control unit 15' which may then be arranged, for instance, around the interconnecting element or on a leg-enclosing socket.

Figure 13:
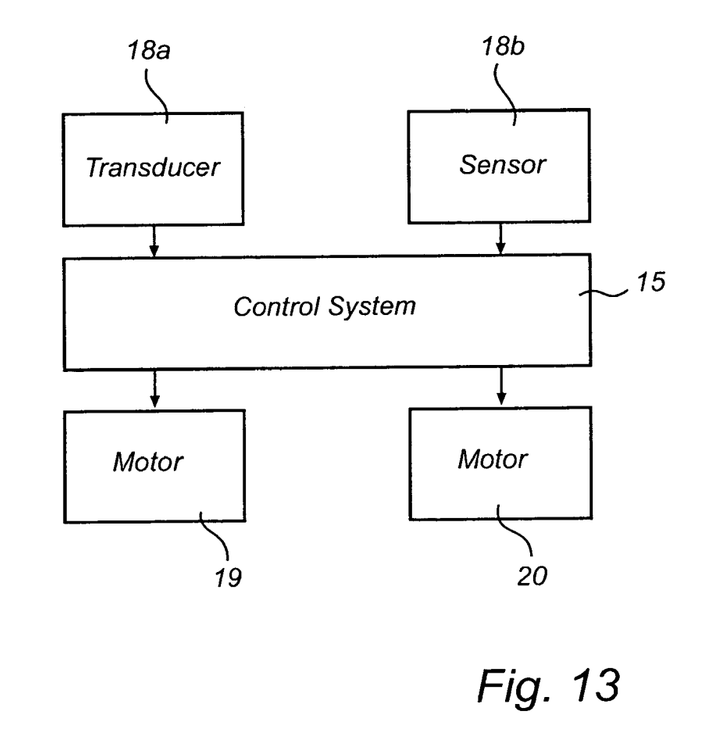
FIG. 13 is a schematic view of a control system for the leg prosthesis of FIG. 1.

FIG. 13 is a schematic view of an embodiment of the leg prosthesis system. The battery drives the hydraulic pump of the drive unit via a motor 19, and a motor 20 for operating the valve of the brake unit. The battery also drives the control system 15 and transducers 18a and sensors 18b of the leg prosthesis system. The control system 15 in turn controls the drive unit and the brake unit and receives input data from transducers 18a and sensors 18b.

It goes without saying that the invention should not be considered limited to the embodiments described above and illustrated in the drawings, with the described variants and alternatives, and can be modified additionally in various ways within the scope of the appended claims.

What is claimed is:

1. A lower limb prosthesis for replacing a missing lower extremity of an individual, said lower limb prosthesis comprising:
   a prosthetic foot member; and
   an ankle module configured to be interposed between the prosthetic foot member and a lower limb member, the ankle module comprising an actuator consisting of a hydraulic assembly including at least one hydraulic cylinder and at least one piston configured to move axially within the at least one hydraulic cylinder as the prosthetic foot member moves relative to the lower limb member such that movement of the at least one piston within the at least one hydraulic cylinder adjusts an angle of the prosthetic foot relative to the lower limb member,
   wherein the hydraulic assembly imparts a force onto the at least one piston during a swing phase in gait to thereby dorsiflex the prosthetic foot relative to the lower limb member.

2. The lower limb prosthesis of claim 1, wherein the ankle module comprises a proximal portion coupled to a distal portion, the proximal portion configured to move relative to the distal portion during a phase in gait.

3. The lower limb prosthesis of claim 1, wherein the hydraulic assembly consists of a single piston configured to move axially within a single cylinder.

4. The lower limb prosthesis of claim 1, wherein the ankle module comprises a pyramid connector configured to couple the ankle module to the lower limb member.

5. The lower limb prosthesis of claim 1, further comprising one or more sensors configured to sense one or more parameters associated with the movement of the prosthetic foot relative to the lower limb member during ambulation.

6. The lower limb prosthesis of claim 5, further comprising a controller configured to receive input data from the one or more sensors corresponding to the one or more sensed parameters, the controller configured to control the operation of a valve in the ankle module to selectively actuate the valve to vary a damping resistance of the hydraulic assembly based at least in part on the one or more sensed parameters.

7. The lower limb prosthesis of claim 1, wherein the force imparted by the hydraulic assembly is a hydraulic force.

8. The lower limb prosthesis of claim 7, wherein the hydraulic force is imparted on a face of the piston to push the piston during the swing phase to dorsiflex the prosthetic foot member.

* * * * *